United States Patent
Hensch

(10) Patent No.: US 9,345,696 B2
(45) Date of Patent: May 24, 2016

(54) METHODS FOR TREATING NICOTINIC ACETYLCHOLINE RECEPTOR ASSOCIATED DISEASES

(75) Inventor: Takao K. Hensch, Newton, MA (US)

(73) Assignees: The Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 88 days.

(21) Appl. No.: 13/294,490

(22) Filed: Nov. 11, 2011

(65) Prior Publication Data

US 2012/0148495 A1 Jun. 14, 2012

Related U.S. Application Data

(60) Provisional application No. 61/413,109, filed on Nov. 12, 2010.

(51) Int. Cl.

| | |
|---|---|
| *A61K 31/445* | (2006.01) |
| *A61P 27/02* | (2006.01) |
| *A61P 25/00* | (2006.01) |
| *A61K 31/55* | (2006.01) |
| *A61K 31/713* | (2006.01) |
| *A61K 31/00* | (2006.01) |
| *A61K 45/06* | (2006.01) |
| *G01N 33/74* | (2006.01) |
| *G01N 33/566* | (2006.01) |
| *C12N 5/079* | (2010.01) |
| *C12Q 1/68* | (2006.01) |
| *A61K 49/00* | (2006.01) |
| *G01N 21/64* | (2006.01) |
| *G01N 21/78* | (2006.01) |
| *A61P 25/18* | (2006.01) |

(52) U.S. Cl.
CPC ............. *A61K 31/445* (2013.01); *A61K 31/00* (2013.01); *A61K 31/55* (2013.01); *A61K 31/713* (2013.01); *A61K 45/06* (2013.01); *G01N 33/74* (2013.01); *G01N 2800/16* (2013.01); *G01N 2800/30* (2013.01); *G01N 2800/7057* (2013.01)

(58) Field of Classification Search
CPC ... A61K 39/395; A61K 31/55; A61K 31/713; A61K 49/00; A61K 31/445; A61P 27/02; A61P 25/00; A61P 25/18; G01N 33/566; G01N 21/64; G01N 21/78; C12N 5/079; C12Q 1/68
USPC ........... 514/284, 44; 424/9.2, 130.1; 435/375, 435/6.12, 6.11, 7.1; 436/501
See application file for complete search history.

(56) References Cited

U.S. PATENT DOCUMENTS

| | | | |
|---|---|---|---|
| 6,273,092 B1 * | 8/2001 | Nolan | 128/898 |
| 2004/0259844 A1 * | 12/2004 | Nolan | 514/78 |
| 2008/0167343 A1 * | 7/2008 | Ieni et al. | 514/319 |

OTHER PUBLICATIONS

Kilo I. Chatzistefanou and Monte D. Mills, The Role of Drug Treatment in Children with Strabismus and Amblyopia, Paediatr Drugs Mar.-Apr. 2000; 2 (2): 91-100.*

* cited by examiner

*Primary Examiner* — Sarah Pihonak
*Assistant Examiner* — Jason A Deck
(74) *Attorney, Agent, or Firm* — Fish & Richardson P.C.

(57) ABSTRACT

The present invention provides methods and compositions for treating subjects suffering from a disorder associated with a nicotinic acetylcholine receptor (nAChR), methods for treating a subject having a disorder that would benefit from an increase in neural plasticity, and methods for modulating the plasticity of the primary visual cortex in subjects by modulating the expression, stability, and/or activity of Lynx1.

15 Claims, 8 Drawing Sheets

METHODS FOR TREATING NICOTINIC ACETYLCHOLINE RECEPTOR ASSOCIATED DISEASES

RELATED APPLICATIONS

This application claims the benefit of and priority to U.S. Provisional Patent Application Ser. No. 61/413,109, filed on Nov. 12, 2010, the entire contents of which are incorporated herein by this reference.

STATEMENT REGARDING FEDERALLY SPONSORED RESEARCH OR DEVELOPMENT

This invention was made with Government support under grant number 1DP1OD003699-01 awarded by the National Institutes of Health. The government, therefore, has certain rights in the invention.

SEQUENCE LISTING

The instant application contains a Sequence Listing which has been submitted via EFS-Web and is hereby incorporated by reference in its entirety. The ASCII copy of the Sequence Listing, created on Nov. 10, 2011, is named SeqList.txt, and is 26,993 bytes in size.

BACKGROUND OF THE INVENTION

The juvenile brain exhibits a high capacity for plasticity and repair that is severely restricted in adulthood. In the juvenile brain, there is a biological "critical period," when the brain is extraordinarily adaptable. The older brain, however, instead of easily re-molding itself to accommodate new kinds of inputs, is more constrained. This waxing and waning of cortical plasticity during a postnatal critical period serves to consolidate neural circuits and behavior, but in turn limits recovery of function in the adult brain.

For example, discordant vision through the two eyes during an early critical period results in the enduring loss of visual acuity (amblyopia) that reflects aberrant circuit remodeling within primary visual cortex (V1). Amblyopia, which affects 2 to 4% of the human population, exhibits little recovery in adulthood (H. Morishita, T. K. Hensch, Curr. Opin. Neurobiol. 18, 101 (2008)).

Thus, experience-dependent brain plasticity declines after an early critical period during which circuits are established. Loss of plasticity with closure of the critical period limits improvement of function in adulthood, but the mechanisms that change the brain's plasticity remain poorly understood.

While many processes contribute to this change in the brain's learning potential, there is evidence suggesting that some of the changes are brought about by the gradual accumulation of molecules that limit the brain's adaptability. It is believed that rather than silencing neurons outright, these molecules help hold them in check, suppressing their tendency to grow and otherwise change with experience. The only molecules previously reported to play a role in closing the critical period are related to axonal growth inhibition, such as chondroitin sulfate proteoglycans and the myelin-signaling proteins NgR and PirB (T. Pizzorusso et al., Science 298, 1248 (2002); A. W. McGee, Y et al., Science 309, 2222 (2005); J. Syken, T., et al., Science 313, 1795 (2006)).

Accordingly, there is a need in the art for the identification of molecules that restrict adult plasticity, modulation of which would be of benefit to injured or dysfunctional adults to permit recovery of neurological performance.

SUMMARY OF THE INVENTION

The present invention is based, at least in part, on the discovery that Lynx1 expression maintains the stability of mature cortical networks in the presence of cholinergic innervation, thus, preventing plasticity in the adult brain. In particular, it has been discovered that an increase in expression of Lynx1 protein prevents experience-dependent brain plasticity in the primary visual cortex of mice late in life and that inhibition of Lynx1 activity enhances nicotinic acetylcholine receptor signaling. Accordingly, the present invention provide methods for treating subjects suffering from a disorder associated with a nicotinic acetylcholine receptor (nAChR), methods for treating a subject having a disorder that would benefit from an increase in neural plasticity, and methods for modulating the plasticity of the primary visual cortex in subjects by modulating the expression and/or activity of Lynx1.

In one aspect, the present invention provides methods for treating a subject suffering from a disorder associated with a nicotinic actylcholine receptor. The methods include modulating the levels of Lynx 1 in the subject, thereby treating the subject suffering from a disorder associated with a nicotinic actylcholine receptor.

In another aspect, the present invention provides methods for treating a subject suffering from a disorder associated with a nicotinic actylcholine receptor. The methods include administering to the subject a moiety which modulates the levels of Lynx1 in said subject, thereby treating the subject suffering from a disorder associated with a nicotinic actylcholine receptor.

In another aspect, the present invention provides methods for treating a subject having a disorder that would benefit from an increase in neural plasticity. The methods include administering to the subject a moiety which modulates the levels of Lynx1 in said subject, thereby treating the subject having a disorder that would benefit from an increase in neural plasticity.

In another aspect, the present invention provides methods for modulating the plasticity of a population of neural cells. The methods include contacting the population of neural cells with a moiety that modulates the levels of Lynx 1, thereby modulating the plascticity of a population of neural cells.

In one embodiment, the moiety is a small molecule, such as Aricept® and Reminyl®. In other embodiments, the moiety is an RNAi, such as a sdRNAi, or an antibody or fragment or derivative thereof.

In one embodiment, the moiety is administered locally.

In one embodiment, the methods of the invention further comprise administering to the subject a cholinesterase inhibitor, such as, Aricept® and Reminyl®.

The disorder associated with a nicotinic actylcholine receptor may be an ophthalmic disorder, such as amblyopia, a mental illness, such as autism and schizophrenia, or stroke.

In one embodiment, the levels of Lynx 1 in said subject are decreased. In another embodiment, the levels of Lynx1 in said subject are increased.

In one embodiment, the subject is a human.

In one aspect, the present invention provides methods modulating the plasticity of the primary visual cortex in a subject. The methods include modulating the levels of Lynx1 in the subject, thereby modulating the plasticity of the primary visual cortex in the subject.

In another aspect, the present invention provides methods for modulating the plasticity of the primary visual cortex in a subject. The methods include administering to the subject a moiety which modulates the levels of Lynx1 in the subject, thereby modulating the plasticity of the primary visual cortex in said subject.

In yet another aspect, the present invention provides methods for identifying a compound useful for treating a subject that would benefit from an increase in neural plasticity. The methods include providing an indicator composition, contacting the indicator composition with a test compound, determining the effect of a test compound on the expression and/or activity of Lynx1, and selecting a compound which modulates the expression and/or activity of Lynx1, thereby identifying a compound useful for treating a subject that would benefit from an increase in neural plasticity.

In another aspect, the present invention provides methods for identifying a compound useful for treating a subject that would benefit from an increase in neural plasticity. The methods include administering a test compound to a non-human animal model of neural plasticity, determining the effect of a test compound on the expression and/or activity of Lynx1, and selecting a compound which modulates the expression and/or activity of Lynx1, thereby identifying a compound useful for treating a subject that would benefit from an increase in neural plasticity.

In one aspect, the present invention provides compositions. The compositions include an inhibitor of Lynx1, and instructions for use for treating a subject suffering from a disorder associated with a nicotinic actylcholine receptor, such as an ophthalmic disorder, such as amblyopia, a mental illness, such as autism and schizophrenia, or stroke.

In another aspect, the present invention provides compositions which include an inhibitor of Lynx1, and instructions for use for treating a subject having a disorder that would benefit from an increase in neural plasticity, such as an ophthalmic disorder, such as amblyopia, a mental illness, such as autism and schizophrenia, or stroke.

In another aspect, the present invention provides compositions which include an inhibitor of Lynx1, and instructions for use for modulating the plasticity of the primary visual cortex.

Other features and advantages of the invention will be apparent from the following detailed description and claims.

DETAILED DESCRIPTION OF THE INVENTION

Figure 1:
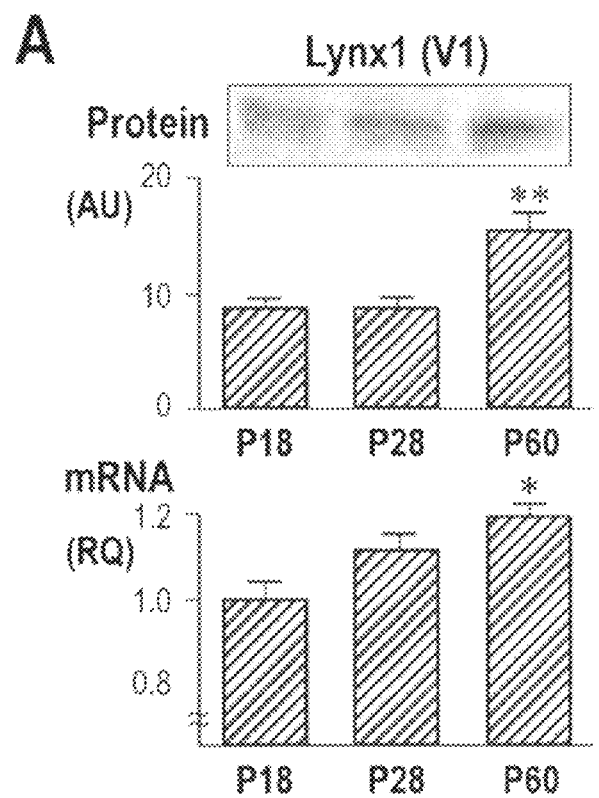
FIGS. 1A-1E depict that Lynx1 expression increases in adulthood to limit visual plasticity. (A) Expression of Lynx1 protein (top) and mRNA (bottom) across the critical period (CP) (pre-CP: P18; CP: P28; post-CP: P60). $**P<0.01$, $*P<0.05$, oneway analysis of variance. AU, arbitrary units; RQ, relative quantification. Data are shown as the mean±SEM. (B) In situ hybridization of Lynx1 in adult V1 (top) and LGN (bottom). Scale bar, 100 mm (C) Adult V1 plasticity paradigm by short-term MD (Ad-MD). (D) Ad-MD shifts the ocular dominance distribution of Lynx1 knockout (KO) mice [bottom; contralateral bias index (CBI)=0.55, 216 cells, 8 mice], but not in wild-type (WT) mice (top; CBI=0.68, 231 cells, 9 mice). KO versus WT: $P<0.0001$, $X^2$ test. (E) Cumulative probability of quantified spike response after Ad-MD confirms shifted ocular dominance scores for Lynx1 KO (blue filled circles), compared to WT (gray filled circles) ($**P<0.005$, Kolmogorov-Smirnov test) or no MD (blue open circles, KO, 93 cells; gray open circles, WT, 82 cells; $P=0.75$, Kolmogorov-Smirnov test).
Figure 1:
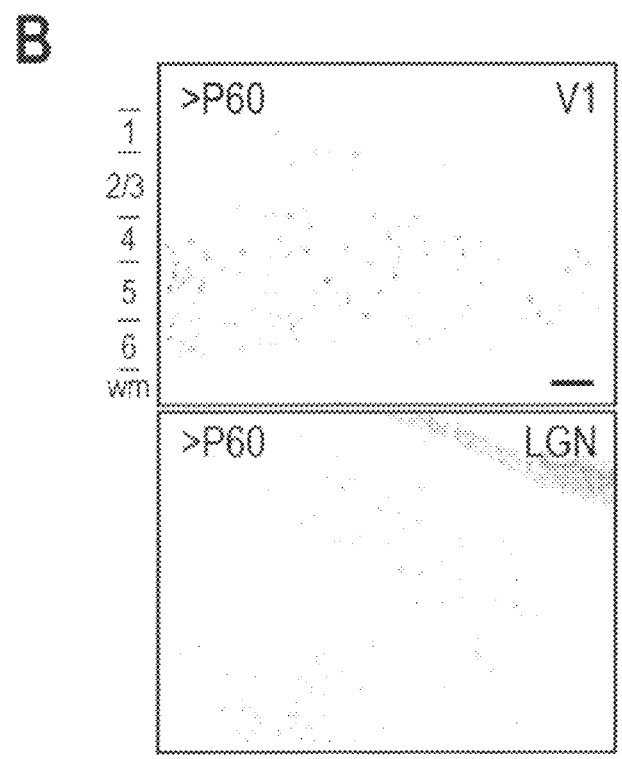
Figure 1:
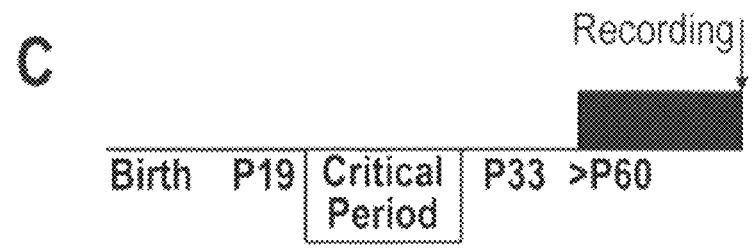
Figure 1:
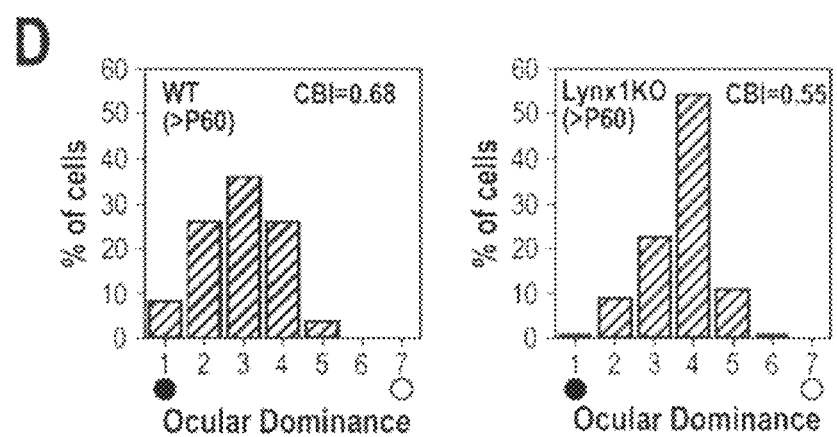
Figure 1:
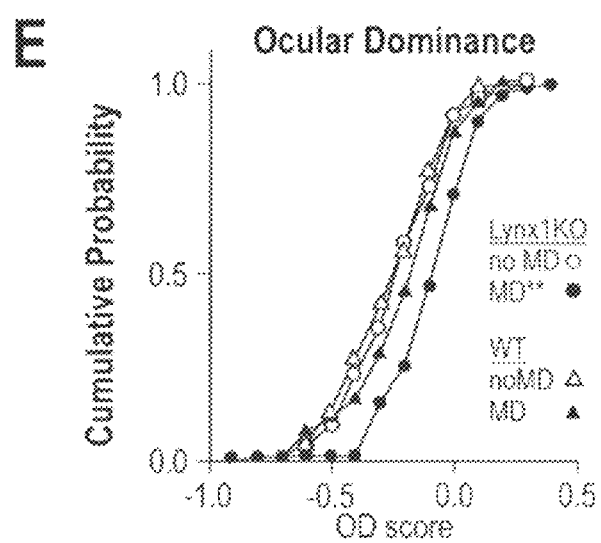

The present invention is based, at least in part, on the discovery that Lynx1 expression maintains the stability of mature cortical networks in the presence of cholinergic innervation, thus, preventing plasticity in the adult brain. In particular, it has been discovered that an increase in expression of Lynx1 protein prevents experience-dependent brain plasticity in the primary visual cortex of mice late in life and that inhibition of Lynx1 activity enhances nicotinic acetylcholine receptor signaling. Accordingly, the present invention provide methods for treating subjects suffering from a disorder associated with a nicotinic acetylcholine receptor (nAChR), methods for treating a subject having a disorder that would benefit from an increase in neural plasticity, and methods for modulating the plasticity of the primary visual cortex in subjects by modulating the expression and/or activity of Lynx1.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

The term "Lynx1", also known as "Ly6/Nuerotoxin 1" and "SLURP2", refers to the endogenous prototoxin similar to α-bungarotoxin in snake venom which binds to the nicotinic acetylcholine receptor (nAChR), such as the major central subunits α4β2 heteromers or α7 homomers, to reduce their sensitivity to acetylcholine. Lynx1 is a member of the Ly-6/neurotoxin gene family, a group of lymphocyte antigens that attach to the cell surface by a glycosylphosphatidylinositol anchor and have a unique structure showing conserved 8-10 cysteine residues with a characteristic spacing pattern. Functional analysis indicates that this protein is not a ligand or neurotransmitter but has the capacity to enhance nicotinic acetylcholine receptor function in the presence of acetylcholine.

There are five alternative transcripts and isoforms of Lynx 1, the nucleotide and amino acid sequences of which are known and may be found in, for example, GenBank Accession Nos. GI:212286119 (SEQ ID NOs.:1 and 2), GI:94538331 (SEQ ID NOs.:3 and 4), GI:29294642 (SEQ ID NOs.:5 and 6), GI:94538332 (SEQ ID NOs.:7 and 8), and GI:94538333 (SEQ ID NOs.:9 and 10), the entire contents of all of which are incorporatd herein by reference.

A "moiety that modulates the level of Lynx 1", an "agent that modulates the level of Lynx 1", or a "modulator of Lynx1" is any compound or molecule that modulates the mRNA expression and/or protein expression of Lynx1; and/or the mRNA and/or protein stability of Lynx1; and/or the biological activity of Lynx1. Exemplary agents suitable for use in the methods of the invention include interfering nucleic acid molecules (e.g., antisense RNAs, sdRNAs, and siRNAs), intracellular antibodies, inhibitory peptides, or small molecules. Agents suitable for use in the methods of the invention are discussed in detail below.

The term "level of Lynx1" includes levels of Lynx1 mRNA or cDNA, and/or protein concentration, expression, activity, function, or stability of Lynx1 protein, DNA, mRNA, or cDNA. In one embodiment, the term "level" as used herein refers to the measurable quantity of Lynx1. The amount may be either (a) an absolute amount as measured in molecules, moles or weight per unit volume or cells or (b) a relative amount, e.g., measured by densitometric analysis.

As used herein, the various forms of the term "modulate" include stimulation (e.g., increasing or upregulating a particular response or activity) and inhibition (e.g., decreasing or downregulating a particular response or activity).

As used herein, the term "inhibit" refers to a decrease in expression, stability, and/or a biological activity of Lynx1. For example, the term "inhibit" refers to the ability to decreasing or downmodulating the expression, stability, and/or activity of Lynx1 as described herein.

As used herein, the term "stimulate" refers to an increase in expression, stability and/or a biological activity of Lynx1. For example, the term "stimulate" refers to the ability to increasing or upmodulating the expression, stability, and/or activity of Lynx1 as described herein.

The term "subject" is used herein to refer to an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, and a whale), a bird (e.g., a duck or a goose), and a shark. In an embodiment, the subject is a human, such as a human being treated or assessed for a disease, disorder or condition, a human at risk for a disease, disorder or condition, a human having a disease, disorder or condition, and/or human being treated for a disease, disorder or condition as described herein. In one embodiment, the subject is about 1, 2, 3, 4, 5, 6, 7, 8, 9, or 10 years of age. In another embodiment, the subject is about 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100 years of age. Values and ranges intermediate to the above recited ranges are also intended to be part of this invention. In addition, ranges of values using a combination of any of the above-recited values as upper and/or lower limits are intended to be included.

The term "administering" includes any method of delivery of a pharmaceutical composition or moiety into a subject's system or to a particular region in or on a subject. In certain embodiments, a moiety is administered intravenously, intramuscularly, subcutaneously, intradermally, intranasally, orally, transcutaneously, intrathecal, intravitreally, intracerebral, or mucosally.

In one embodiment, the administration of the moiety is a local administration, e.g., intravitreal administration and administration locally in the brain, e.g., administration to the visual cortex, e.g., the primary visual cortex, or local administration to any area of the brain that is in need of an increase in neural plasticity, e.g., administration to the neocortex, administration to the auditory cortex, administration to the motor cortex, and/or administration of the somatosensory cortex.

As used herein, the term "contacting" (i.e., contacting a cell, e.g., a host cell, or a subject with a moiety) includes incubating the moiety and the, e.g., cell, together in vitro (e.g., adding the moiety to cells in culture) as well as administering the moiety to a subject such that the moiety and cells or tissues of the subject are contacted in vivo.

As used herein, the terms "treating" or "treatment" refer to a beneficial or desired result including, but not limited to, alleviation or amelioration of one or more symptoms, diminishing the extent of a disorder, stabilized (i.e., not worsening) state of a disorder, amelioration or palliation of the disorder, whether detectable or undetectable. "Treatment" can also mean prolonging survival as compared to expected survival in the absence of treatment. For example, for amblyopia, the disorder may be treated by improving vision in the amblyopic eye. For autism, the disorder may be treated by decreasing one or more symptoms of irritability, lethargy, and hyperactivity, inadequate eye contact, and inappropriate speech. For schizophrenia, the disorder may be treated by decreasing the level or frequency of hallucinations, delusions, inability to focus attention, as well as other cognitive disturbances.

As used herein, the term "effective amount" refers to the amount of a therapy, which is sufficient to reduce or ameliorate the severity and/or duration of a disorder or one or more symptoms thereof, inhibit or prevent the advancement of a disorder, cause regression of a disorder, inhibit or prevent the recurrence, development, onset or progression of one or more symptoms associated with a disorder, detect a disorder, or enhance or improve the prophylactic or therapeutic effect(s) of another therapy (e.g., prophylactic or therapeutic agent). An effective amount can require more than one dose.

"Plasticity" and "neural plasticity" as used herein refer to the ability of the central nervous system to reorganize its connections functionally and structurally in response to changes in environmental experience, e.g., sight, touch, smell, feel, as part of the adaptive development of neuronal circuitry.

Nicotinic acetylcholine receptors (nAChRs) are pentameric integral membrane proteins that are members of a family of ligand-gated ion channel receptors, which include the $GABA_A$, glycine, and serotonin $5HT3_{A\ and\ B}$ receptors. The nAChRs mediate "fast" synaptic transmission on a millisecond time frame, rapidly changing the membrane potential. Each of the 5 constituent receptor polypeptide subunits share a common motif that includes a large extracellular N-terminal hydrophilic domain, 3 transmembranous hydrophobic domains (termed M1-M3), an intracellular loop of variable size that contains consensus sequences of amino acids for enzymatic phosphorylation, and a C-terminal M4 transmembranous hydrophobic domain; the M2 transmembranous domains of each of the 5 receptor polypeptide subunits are aligned to create a potential channel, whose opening is gated by acetylcholine. These receptors are assembled from an extensive family of subunits. In vertebrates, the 17 nAChR subunits ($\alpha1$-$\alpha10$, $\beta1$-$\beta4$, $\gamma$, $\delta$ and $\epsilon$) can assemble into a variety of pharmacologically distinct receptor subtypes.

There are muscle-type nAChRs and neuronal nAChRs. There is considerable diversity among the sub-family of neuronal nAChRs.

As used herein, the term "disorder associated with a nicotinic actylcholine receptor" refers to any disorder or injury in which nAChR signaling is abnormal, in which there is a depletion of cholinergic neurons, and/or in which there is reduction in the number of nicotinic ACh receptors. Such disorders include, but are not limited to, ophthalmic disorders, mental illness, stroke, and cognitive disorders. Non-limiting examples of ophthalmic disorders include amblyopia or lazy eye. Non-limiting examples of mental illness include autism and schizophrenia. Non-limiting examples of cognitive disorders include, for example, senile dementia of the Alzheimer type, and cognitive impairment due to aging or traumatic brain injury.

As used herein, the term "a subject having a disorder that would benefit from an increase in neural plasticity" refers to subject having a disorder or injury that would benefit from an increase in the functional and structural reorganization of central nervous system connections in response to changes in environmental experience. Such disorders also include, but are not limited to, ophthalmic disorders, mental illness, stroke, and cognitive disorders. Non-limiting examples of ophthalmic disorders include amblyopia or lazy eye. Non-limiting examples of mental illness include autism and schizophrenia. Non-limiting examples of cognitive disorders include, for example, cognitive impairment due to aging or traumatic brain injury.

The "visual cortex" of the brain is that part of the cerebral cortex responsible for processing visual information. It is located in the occipital lobe of the brain. The term "primary visual cortex" (also known as the "striate cortex" or "V1") is anatomically equivalent to Brodmann area 17, or BA17. The primary visual cortex, V1, is the koniocortex (sensory type) located in and around the calcarine fissure in the occipital lobe. Each hemisphere's V1 receives information directly from its ipsilateral lateral geniculate nucleus. Each V1 transmits information to two primary pathways, called the dorsal stream and the ventral stream. The dorsal stream begins with V1, goes through Visual area V2, then to the dorsomedial area and Visual area MT (also known as V5) and to the posterior parietal cortex. The dorsal stream, sometimes called the "Where Pathway" or "How Pathway", is associated with motion, representation of object locations, and control of the eyes and arms, especially when visual information is used to guide saccades or reaching. The ventral stream begins with V1, goes through visual area V2, then through visual area V4, and to the inferior temporal cortex. The ventral stream, sometimes called the "What Pathway", is associated with form recognition and object representation. It is also associated with storage of long-term memory.

II. Methods of the Invention

The present invention provides methods for treating subjects suffering from a disorder associated with a nicotinic acetylcholine receptor (nAChR), methods for treating a subject having a disorder that would benefit from an increase in neural plasticity, and methods for modulating the plasticity of the primary visual cortex in a subject.

In some embodiments, the methods of the invention include modulating the levels of Lynx1 in the subject. In other embodiments, the methods of the invention include administering to the subject a moiety which modulates the levels of Lynx1 in the subject.

The present invention also provides methods for modulating the plasticity of a neural connection in a population of neural cells. The methods include contacting a population of neural cells with a moiety that modulates, e.g., inhibits, the expression, stability, and/or activity of Lynx 1.

The methods may be performed by contacting a cell (or a plurality of cells) with the moiety in vitro and then, e.g., the cells can be administered to an organism in vivo, or, alternatively, the moiety may be administered to a subject (e.g., parenterally or locally) such that the cells are contacted with the moiety in vivo.

Disorders that would benefit from the methods of the invention include, for example, ophthalmic disorders (i.e., disorders of the eye), such as amblyopia; mental illneses, such as schizophrenia, autism; and cognitive disorders associated with, for example, stroke, aging, and/or traumatic or acquired brain injury.

"Amblyopia", "strabismic amblyopia", "lazy eye" is a disorder of the visual system that is characterized by a vision deficiency in an eye that is otherwise physically normal, or out of proportion to associated structural abnormalities of the eye. It has been estimated to affect 1-5% of the population. The term lazy eye may also be used to describe strabismus ("crossed" eye). However, while a crossed eye may become amblyopic, not all crossed eyes are amblyopic nor are all amblyopic eyes crossed.

A subject having amblyopia may be diagnosed by one or skill in the art, such as an orthoptists, ophthalmologists and optometrists, using, for example, a cover test. If the eye being tested is the strabismic eye, then it will fixate on the object after the "straight" eye is covered, as long as the vision in this eye is good enough. If the "straight" eye is being tested, there will be no change in fixation, as it is already fixated. Depending on the direction that the strabismic eye deviates, the direction of deviation may be assessed. A Hirschberg test where a flashlight is shone in the patient's eye may also be used. When the patient is looking at the light, a reflection can be seen on the front surface of the pupil. If the eyes are properly aligned with one another, then the reflection will be in the same spot of each eye. Therefore, if the reflection is not in the same place in each eye, then the eyes aren't properly aligned.

A "mental disorder" or "mental illness" is a psychological or behavioral pattern generally associated with subjective distress or disability that occurs in an individual, and which is not a part of normal development or culture. Such a disorder may consist of a combination of affective, behavioural, cognitive and perceptual components.

In one embodiment, the methods of the invention may be used to treat schizophrenia. "Schizophrenia" is a mental disorder characterized by a disintegration of thought processes and of emotional responsiveness. It most commonly manifests itself as auditory hallucinations, paranoid or bizarre delusions, or disorganized speech and thinking, and it is accompanied by significant social or occupational dysfunction. The onset of symptoms typically occurs in young adulthood, with a global lifetime prevalence of about 0.3-0.7%. Diagnosis is based on criteria in either the American Psychiatric Association's Diagnostic and Statistical Manual of Mental Disorders, version DSM-IV-TR, or the World Health Organization's International Statistical Classification of Diseases and Related Health Problems, the ICD-10. These criteria use the self-reported experiences of the person and reported abnormalities in behavior, followed by a clinical assessment by a mental health professional.

Numerous studies have shown that there is a decrease in nicotinic acetylcholine receptor expression and/or activity. Accordingly, a subject having schizophrenia will benefit from treatment with a moiety that modulates, e.g., inhibits, the expression and/or activity of Lynx1 to increase, e.g., neural plasticity and/or nicotinic acetylcholine receptor signaling.

"Autism" is a disorder of neural development characterized by impaired social interaction and communication, and by restricted and repetitive behavior. A diagnosis of autism may be made using one or more of several diagnostic instruments. For example, the Autism Diagnostic Interview-Revised (ADI-R) is a semistructured parent interview, and the Autism Diagnostic Observation Schedule (ADOS) uses observation and interaction with the child. The Childhood Autism Rating Scale (CARS) is used widely in clinical environments to assess severity of autism based on observation of children. Autism is defined in the DSM-IV-TR as exhibiting at least six symptoms total, including at least two symptoms of qualitative impairment in social interaction, at least one symptom of qualitative impairment in communication, and at least one symptom of restricted and repetitive behavior. Sample symptoms include lack of social or emotional reciprocity, stereotyped and repetitive use of language or idiosyncratic language, and persistent preoccupation with parts of objects. Onset must be prior to age three years, with delays or abnormal functioning in either social interaction, language as used in social communication, or symbolic or imaginative play.

A reduction in protein expression in cortical areas for nicotinic acetylcholine receptors, e.g., the α4 and β2 subunits, in autistic subjects has been observed. Accordingly, a subject having autism will benefit from treatment with a moiety that modulates, e.g., inhibits, the expression and/or activity of Lynx1 to increase, e.g., neural plasticity and/or nicotinic acetylcholine receptor signaling.

A "cognitive disorder" is a mental disorder that may be short or long term interruption, in basic cognitive functions, such as memory processing, perception, problem solving and language. In one embodiment a cognitive disorder is schizophrenia. In another embodiment, a cognitive disorder is a stroke. In yet another embodiment, a cognitive disorder is Alzheimer's disease.

"Alzheimer's disease" is characterised by a profound loss of memory and cognitive functions caused by a severe depletion of cholinergic neurons, i.e. neurons that release acetylcholine. A reduction in the number of nicotinic acetylcholine receptors has also been observed with the progression of Alzheimer's disease. Neurons in the cortex die with the progression of Alzheimer's disease due to, for example, lack of stimulation of the nAChRs. Accordingly, a subject having Alzheimer's disease will benefit from treatment with a moiety that modulates, e.g., inhibits, the expression and/or activity of Lynx1 to increase, e.g., neural plasticity and/or nicotinic acetylcholine receptor signaling.

Degneration of the cholinergic nervous system is also observed in healthy aged subjects and rats. Therefore, a subject having Alzheimer's disease will benefit from treatment with a moiety that modulates, e.g., inhibits, the expression and/or activity of Lynx1 to increase, e.g., neural plasticity and/or nicotinic acetylcholine receptor signaling.

Diagnosis of cognitive disorders is typically clinically based on patient history, collateral history from relatives, and clinical observations, based on the presence of characteristic neurological and neuropsychological features and the absence of alternative conditions. Advanced medical imaging with computed tomography (CT) or magnetic resonance imaging (MRI), and with single photon emission computed tomography (SPECT) or positron emission tomography (PET) can be used. In the case of Alzheimer's disease, these methods may be used to exclude other cerebral pathology or subtypes of dementia. Moreover, they may predict conversion from prodromal stages (mild cognitive impairment) to Alzheimer's disease. Assessment of intellectual functioning including memory testing can further be used.

As used herein, the term "stroke" refers to the art recognized pathological condition in which impairment of consciousness and neurological symptom(s) are acutely induced by a cerebrovascular disorder, which includes intracerebral hemorrhages (hypertensive intracerebral hemorrhage and the like), cerebral infarction, transient ischemic attack, subarachnoid hemorrhage, cerebral thrombosis (atherothrombotic cerebral infarction and the like), cerebral embolism (cardiogenic cerebral embolism and the like) and lacunar infarction. Low administration of nicotine which activates nicotinic acetylcholine receptors has been observed to improve outcome of subjects having a stroke. Accordingly, a subject having a stoke will benefit from treatment with a moiety that modulates, e.g., inhibits, the expression and/or activity of Lynx1 to increase, e.g., neural plasticity and/or nicotinic acetylcholine receptor signaling.

Use of an "effective amount" of the moieties of the present invention (and therapeutic compositions comprising such agents) is an amount effective, at dosages and for periods of time necessary to achieve the desired result.

For example, an effective amount of a moiety may vary according to factors such as the disease state, age, sex, reproductive state, and weight, and the ability of the agent to elicit a desired response in the organism. Dosage regimens may be adjusted to provide the optimum response. For example, several divided doses may be provided daily or the dose may be proportionally reduced as indicated by the exigencies of the situation.

The moieties of the present invention may be administered in an amount effective to achieve a desired result and/or at a dose that is sufficient to elicit an increase in neural plasticity in a subject based on the mode of administration and without significant adverse side effects.

Dose administration can be repeated depending upon the pharmacokinetic parameters of the dosage formulation and the route of administration used. It is also provided that certain formulations containing a moiety useful in the methods of the invention are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, olyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the organism by employing procedures well known in the art. The formulations can also contain substances that diminish proteolytic degradation and/or substances which promote absorption such as, for example, surface active agents.

It is especially advantageous to formulate compositions, e.g., parenteral compositions, in dosage unit form for ease of administration and uniformity of dosage. Dosage unit form as used herein refers to physically discrete units suited as unitary dosages for the organisms to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individual organisms. The specific dose can be readily calculated by one of ordinary skill in the art, e.g., according to the approximate weight, e.g., body weight, or surface area of the organism or the volume of space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual organism, the severity of the organism's symptoms, and the chosen route of administration.

Toxicity and therapeutic efficacy of such compounds can be determined by standard pharmaceutical procedures in cell cultures or experimental plant and/or animal models, e.g. for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method for the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The agents or pharmaceutical compositions of the present invention can be administered by any suitable route known in the art including for example intravenous, subcutaneous, intramuscular, transdermal, intrathecal, intravitreally, or intracerebral administration to cells in ex vivo treatment protocols, or delivered on a surface, e.g., a biocompatible surface. Administration can be either rapid as by injection or over a period of time as by slow infusion or administration of slow release formulation.

In one embodiment, administration of a moiety of the invention is local administration, such as intracerebroventricular (into the cerebral ventricles) administration, intravitreal administration, administration to the visual cortex, e.g., the primary visual cortex, or administration to any area of the brain that is in need of an increase in neural plasticity, e.g., administration to the neocortex, administration to the auditory cortex, administration to the motor cortex, and/or administration of the somatosensory cortex.

In the methods of the invention in which a moiety is a cholinesterase inhibitor, such as Aricept®, a suitable dose may be 2 mg, 2.5 mg, 5 mg or 10 mg, once per day. In the methods of the invention in which a moiety is a cholinesterase inhibitor, such as Reminyl®, a suitable dose may be 2, 4, 6, or 8, 10, 12, 14, 16, 18, 20, or 24, once per day.

The methods provided herein can be practiced in combination or sequentially with any other additional methods and/or treatment currently used to treat a disorder as described herein. For example, methods used to treat amblyopia may further include perceptual learning methods or visual tasks such as action-packed video games, prescription lenses, prisms, vision therapy, eye patching, and/or botox. Methods used to treat a cognitive disorder, such as schizophrenia may further include treatment with antipsychotics, such as clozapine, and psychosocial interventions, such as family therapy, assertive community treatment, supported employment, cognitive remediation, skills training, cognitive behavioral therapy (CBT), token economic interventions, and psychosocial interventions for substance use and weight management. Methods used to treat Alzheimer's disease may include, for example, pharmaceutical, e.g., acetylcholinesterase inhibitors, an NMDA receptor antagonist (e.g., noncompetitive NMDA receptor antagonists), glutamate, antipsychotics, psychosocial and caregiving. Methods used to treat stroke may include physical rehabilitation. Methods used to treat autism include, for example, treatment with antidepressants, stimulants, and/or antipsychotics, behavior therapy, structured teaching, speech and language therapy, social skills therapy, and occupational therapy.

In the methods of the invention, treatment of a subject about 6 to about 20, about 7 to about 19, about 8 to about 17 years old having, for example, an ophthalmic disorder, such as, amblyopia, may include, patching the unaffected eye daily for about 0.5, about 1, about 1.5, about 2, about 2.5, about 3, about 3.5, about 4, about 4.5, about 5, about 5.5, about 6, about 6.5, about 7, about 7.5, or about 8 hours and use of about 1.5, about 2, about 2.5, about 3, about 3.5, about 4, about 4.5, or about 5 mg daily of a cholinesterase inhibitor, e.g., donepezil (Aricept®), for about 5, about 6, about 7, about 8, about 9, about 10, about 11, about 12, about 13, about 14, about 15, about 16, about 17, about 18, about 19, or about 20 weeks.

In one embodiment, a subject between about 8 and about 17 years of age and having an ophthalmic disorder, such as amblyopia, has the unaffected eye patched for about 2 hours per day and is administered about 2.5 mg of a cholinesterase cholinesterase inhibitor, e.g., donepezil (Aricept®) for 12 weeks.

Treatment of a subject greater than about 18 years of age having, for example, an ophthalmic disorder, such as, amblyopia, may include, patching the unaffected eye daily for about 0.5, about 1, about 1.5, about 2, about 2.5, about 3, about 3.5, about 4, about 4.5, about 5, about 5.5, about 6, about 6.5, about 7, about 7.5, or about 8 hours and use of about 1.5, about 2, about 2.5, about 3, about 3.5, about 4, about 4.5, about 5, about 5.5, about 6, about 6.5., about 7, about 7.5, about 8, about 8.5, about 9, about 9.5, or about 10 mg of a cholinesterase inhibitor, e.g., donepezil (Aricept®), for about 5, about 6, about 7, about 8, about 9, about 10, about 11, about 12, about 13, about 14, about 15, about 16, about 17, about 18, about 19, or about 20 weeks.

In one embodiment, a subject greater than about 18 years of age and having an ophthalmic disorder, such as ambylopia, has the unaffected eye patched for about 2 hours per day and is administered about 5 mg of a cholinesterase cholinesterase inhibitor, e.g., donepezil (Aricept®) for 12 weeks.

III. Moieties for Use in the Methods of the Invention

As described herein, an increase of Lynx1 expression prevents neural plasticity, i.e., neural plasticity in the primary visual cortex, late in life as well as enhanced nicotinic acetylcholine receptor signaling. Accordingly, moieties which modulate, e.g., inhibit, Linx1 expression and/or activity and/or molecules which enhance nicotinic acetylcholine receptor signaling, e.g., cholinesterase inhibitors, are useful in the methods of the invention.

In one embodiment, a moiety for use in the methods of the invention is an inhibitory moiety. In one embodiment, an inhibitory moiety is a small molecule, e.g., a small molecule cholinesterase inhibitor. In another embodiment, an inhibitory moiety for use in the methods of the invention is an intracellular binding molecule that acts to specifically inhibit the expression, stability, and/or activity of Lynx1. In another embodiment, an inhibitory moiety for use in the methods of the invention of the invention is a nucleic acid molecule which acts to specifically decrease the expression, stability, and/or activity of Lynx 1. In yet another embodiment, a stimulatory moiety for use in the methods of the invention of the invention is a nucleic acid molecule which acts to specifically increase the expression, stability. and/or activity of Lynx 1.

As used herein, the term "intracellular binding molecule" is intended to include molecules that act intracellularly to inhibit the expression or activity of a protein by binding to the protein or to a nucleic acid (e.g., an mRNA molecule) that encodes the protein. Examples of intracellular binding molecules, described in further detail below, include inhibitory nucleic acids, siRNA molecules, intracellular antibodies, peptidic compounds that inhibit the interaction of Lynx1 with a target molecule (e.g., a nicotinic acetylcholine receptor, e.g., $\alpha_4\beta_2$ heteromers or $\alpha_7$ homomers), and chemical agents that specifically inhibit Lynx1 activity.

The moieties can also be linked or conjugated with agents that provide desirable pharmaceutical or pharmacodynamic properties. For example, a moiety can be stably linked to a polymer such as polyethylene glycol to obtain desirable properties of solubility, stability, half-life and other pharmaceutically advantageous properties. (See for example Davis et al., 1978, *Enzyme Eng* 4: 169-73; Burnham, 1994, *Am J Hosp Pharm* 51: 210-218, which are incorporated by reference).

Furthermore, a moiety can be in a composition which aids in delivery into the cytosol of a cell. For example, the moiety may be conjugated with a carrier moiety such as a liposome that is capable of delivering the peptide into the cytosol of a cell. Such methods are well known in the art (for example see Amselem et al., 1993, *Chem Phys Lipids* 64: 219-237, which is incorporated by reference). Alternatively, the moiety can be modified to include specific transit peptides or fused to such transit peptides which are capable of delivering the inhibitory agent into a cell. In addition, the moiety can be delivered directly into a cell by microinjection.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous Inhibitory agents can also be incorporated into a solid or semi-solid biologically compatible matrix which can be implanted into tissues requiring treatment.

In one embodiment, a moiety of the invention may be administered to a subject as a pharmaceutical composition. In one embodiment, the invention is directed to an active compound (e.g., a inhibitor of Lynx1) and a carrier. Such compositions typically comprise the inhibitory agent, e.g., as described herein or as identified in a screening assay, e.g., as described herein, and a pharmaceutically acceptable carrier. Pharmaceutically acceptable carriers and methods of administration to a subject are described herein.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will preferably be sterile and should be fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

A. Inhibitory Moieties i. Cholinesterase Inhibitors

Cholinesterase inhibitors, also referred to as acetylcholinesterase inhibitors are known in the art. Non-limiting examples of a cholinesterase inhibitors for use in the methods of the invention include donepezil (Aricept™), galantamine (Razadyne™), rivastigmine (Exelon™), Tetrahydroaminoacridine (tacrine) (brand name Cognex™). Other non-limiting examples of cholinesterase inhibitors or acetylcholinesterase inhibitors include any of the following compounds as well as their analogs and pharmaceutically acceptable salts: huperzine A, Green mamba snake (Dendroaspis angusticeps)

toxin fasciculin, metrifonate, heptyl-physostigmine, pyridostigmine, norpyridostigmine, norneostigmine, physostigmine, velnacrine, citicoline, metrifonate, 7-methoxytacrine, eptastigmine, icopezil, ipidacrine, zifrosilone, anseculin, suronacrine, linopiridine, rivastigmine, neostigmine, edrophonium, edrophonium chloride, demacarium ambenonium, physostigmine salicalte, physostigmine sulfate, physostigmine bromide, pralidoxime chloride, obidoxime chloride, trimedoxime bromide, and diacetyl monoxim.

ii. Interfering Nucleic Acid Molecules

The term "interfering nucleic acid molecule" or "interfering nucleic acid" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), self-delivering RNA (sdRNA; see, e.g., U.S. Patent Publication Nos. 200913120341, 200913120315, and 201113069780, the entire contents of all of which are incorporated herein by reference), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression (and, thus, the activity) of a target gene or sequence (e.g., by mediating the degradation or inhibiting the translation of mRNAs which are complementary to the interfering RNA sequence) when the interfering nucleic acid is in the same cell as the target gene or sequence. Interfering nucleic acid thus refers to a single-stranded nucleic acid molecules that are complementary to a target mRNA sequence or to the double-stranded RNA formed by two complementary strands or by a single, self-complementary strand. Interfering nucleic acids may have substantial or complete identity to the target gene or sequence, or may comprise a region of mismatch (i.e., a mismatch motif). The sequence of the interfering nucleic acids can correspond to the full-length target gene, or a subsequence thereof (e.g., the gene for Lynx1, the sequence of which is provided in, for example, SEQ ID NOs.: 1-10). Preferably, the interfering nucleic acid molecules are chemically synthesized. The disclosures of each of the above patent documents are herein incorporated by reference in their entirety for all purposes.

As used herein, the term "mismatch motif" or "mismatch region" refers to a portion of an interfering nucleic acid (e.g., siRNA) sequence that does not have 100% complementarity to its target sequence. An interfering nucleic acid may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

An interfering nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an interfering nucleic acid is an antisense nucleic acid and can hydrogen bond to the sense nucleic acid.

In one embodiment, an interfering nucleic acid of the invention is a "small-interfering RNA" or "an siRNA" molecule. In another embodiment, an interfering nucleic acid molecules of the invention is a "self-delivering RNA" or "sdRNA" molecule. In one embodiment, an interfering nucleic acid of the invention mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein for use in antisense RNA can be employed in molecules that mediate RNAi.

Interfering nucleic acid includes, e.g., siRNA and sdRNA, of about 10-60, 10-50, or 10-40 (duplex) nucleotides in length, more typically about 8-15, 10-30, 10-25, or 10-25 (duplex) nucleotides in length, about 10-24, (duplex) nucleotides in length (e.g., each complementary sequence of the double-stranded siRNA is 10-60, 10-50, 10-40, 10-30, 10-25, or 10-25 nucleotides in length, about 10-24, 11-22, or 11-23 nucleotides in length, and the double-stranded siRNA is about 10-60, 10-50, 10-40, 10-30, 10-25, or 10-25 base pairs in length). siRNA and sdRNA duplexes may comprise 3'-overhangs of about 1 to about 6 nucleotides and 5'-phosphate termini Examples of siRNA and sdRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA (or sdRNA) molecule. As used herein, the terms "siRNA" and "sdRNA' include RNA-RNA duplexes as well as DNA-RNA hybrids (see, e.g., PCT Publication No. WO 2004/078941).

Preferably, siRNA and sdRNA are chemically synthesized. siRNA and sdRNA can also be generated by cleavage of longer dsRNA (e.g., dsRNA about 5, about 10, about 15, about 20, about 25, or greater nucleotides in length) with the E. coli RNase III or Dicer. These enzymes process the dsRNA into biologically active siRNA (see, e.g., Yang et al., Proc. Natl. Acad. Sci. USA, 99:9942-9947 (2002); Calegari et al., Proc. Natl. Acad. Sci. USA, 99:14236 (2002); Byrom et al., Ambion TechNotes, 10(1):4-6 (2003); Kawasaki et al., Nucleic Acids Res., 31:981-987 (2003); Knight et al., Science, 293:2269-2271 (2001); and Robertson et al., J. Biol. Chem., 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA or sdRNA may be encoded by a plasmid (e.g., transcribed as sequences that automatically fold into duplexes with hairpin loops).

Given the coding strand sequences encoding Lynx1 known in the art and disclosed herein, an interfering nucleic acids of the invention can be designed according to the rules of Watson and Crick base pairing. The interfering nucleic acid molecule can be complementary to the entire coding region of Lynx1 mRNA, but more preferably is an oligonucleotide which is antisense to only a portion of the coding or noncoding region of Lynx1 mRNA. For example, an interfering oligonucleotide can be complementary to the region surrounding the processing site of ubiquitin and Lynx1 mRNA. An interfering RNA oligonucleotide can be, for example, about 5, 10, 15, 20, 25, 30, 35, 40, 45 or 50 nucleotides in length. An interfering nucleic acid of the invention can be constructed using chemical synthesis and enzymatic ligation reactions using procedures known in the art. For example, an interfering nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the interfering nucleic acids include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more interfering nucleic acid molecules can be used. Alternatively, the an interfering nucleic acid can be produced biologically using an expression vector into which a nucleic acid has been subcloned in an antisense orientation (i.e., RNA transcribed from the inserted nucleic acid will be of an antisense orientation to a target nucleic acid of interest).

In yet another embodiment, an interfering nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The interfering nucleic acid molecule can also comprise a 2'-O-methylribonucleotide (Inoue et al. (1987) Nucleic Acids Res. 15:6131-6148) or a chimeric RNA-DNA analogue (Inoue et al. (1987) FEBS Lett. 215:327-330).

In still another embodiment, an interfering nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, Nature 334:585-591) can be used to catalytically cleave Lynx1 mRNA transcripts to thereby inhibit translation of Lynx1 mRNA. A ribozyme having specificity for a Lynx1-encoding nucleic acid can be designed based upon the nucleotide sequence of Lynx1. For example, a derivative of a Tetrahymena L-19 IVS RNA can be constructed in which the nucleotide sequence of the active site is complementary to the nucleotide sequence to be cleaved in a Lynx1-encoding mRNA. See, e.g., Cech et al. U.S. Pat. No. 4,987,071; and Cech et al. U.S. Pat. No. 5,116,742. Alternatively, Lynx1 mRNA can be used to select a catalytic RNA having a specific ribonuclease activity from a pool of RNA molecules. See, e.g., Bartel, D. and Szostak, J. W., 1993, Science 261:1411-1418.

Alternatively, gene expression can be inhibited by targeting nucleotide sequences complementary to the regulatory region of Lynx1 (e.g., the ubiquitin/Lynx1 promoter and/or enhancers) to form triple helical structures that prevent transcription of the ubiquitin/Lynx1 gene in target cells. See generally, Helene, C., 1991, Anticancer Drug Des. 6(6):569-84; Helene, C. et al., 1992, Ann. N.Y. Acad. Sci. 660:27-36; and Maher, L. J., 1992, Bioassays 14(12):807-15.

In yet another embodiment, the inhibitory nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., 1996, Bioorganic & Medicinal Chemistry 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al., 1996, supra; Perry-O'Keefe et al., 1996, Proc. Natl. Acad. Sci. USA 93: 14670-675.

In another embodiment, PNAs of Lynx1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Lynx1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B., 1996, supra). The synthesis of PNA-DNA chimeras can be performed as described in Hyrup B., 1996, supra and Finn P. J. et al., 1996, Nucleic Acids Res. 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA Gag, M. et al., 1989, Nucleic Acid Res. 17: 5973-88). PNA monomers are then coupled in a stepwise manner to produce a chimeric molecule with a 5' PNA segment and a 3' DNA segment (Finn P. J. et al., 1996, supra). Alternatively, chimeric molecules can be synthesized with a 5' DNA segment and a 3' PNA segment (Peterser, K. H. et al., 1975, Bioorganic Med. Chem. Lett. 5: 1119-11124).

In other embodiments, the interfering nucleic acid may include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; PCT Publication No. WO088/09810) or the blood-brain bather (see, e.g., PCT Publication No. WO89/10134). In addition, oligonucleotides can be modified with hybridization-triggered cleavage agents (See, e.g., Krol et al., 1988, *Bio-Techniques* 6:958-976) or intercalating agents. (See, e.g., Zon, 1988, *Pharm. Res.* 5:539-549). To this end, the oligonucleotide may be conjugated to another molecule, (e.g., a peptide, a lipophillic group, hybridization triggered cross-linking agent, transport agent, or hybridization-triggered cleavage agent).

Interfering polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

iii. Intracellular Antibodies

Another type of inhibitory compound or agent that can be used to inhibit the expression and/or activity of Lynx1 protein in a cell is an intracellular antibody specific for Lynx1. The use of intracellular antibodies to inhibit protein function in a cell is known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Letters* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al. and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell.

To prepare an intracellular antibody expression vector, antibody light and heavy chain cDNAs encoding antibody chains specific for the target protein of interest, e.g., Lynx1 protein, is isolated, typically from a hybridoma that secretes a monoclonal antibody specific for Lynx1 protein. Anti-Lynx1 protein antibodies can be prepared by immunizing a suitable subject, (e.g., rabbit, goat, mouse or other mammal) with a Lynx1 protein immunogen. An appropriate immunogenic preparation can contain, for example, recombinantly expressed Lynx1 protein or a chemically synthesized Lynx1 peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes) from a mammal immunized with a Lynx1 protein immunogen as described above, and the culture supernatants of the resulting hybridoma cells are screened to identify a hybridoma producing a monoclonal antibody that binds specifically to the Lynx1 protein. Any of the many well known protocols used for fusing lymphocytes and immortalized cell lines can be applied for the purpose of generating an anti-Lynx1 protein monoclonal antibody (see, e.g., G. Galfre et al. (1977) *Nature*, 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the maf protein are identified by screening the hybridoma culture supernatants for such antibodies, e.g., using a standard ELISA assay.

Alternative to preparing monoclonal antibody-secreting hybridomas, a monoclonal antibody that binds to Lynx1 can be identified and isolated by screening a recombinant combinatorial immunoglobulin library (e.g. an antibody phage display library) with the protein, or a peptide thereof, to thereby isolate immunoglobulin library members that bind specifically to the protein. Kits for generating and screening phage display libraries are commercially available (e.g., the Pharmacia Recombinant Phage Antibody System; and the Stratagene SurfZAP™ Phage Display Kit). Additionally, examples of methods and compounds particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al.

(1991) *Nuc Acid Res* 19:4133-4137; Barbas et al. (1991) *PNAS* 88:7978-7982; and McCafferty et al. *Nature* (1990) 348:552-554.

Once a monoclonal antibody of interest specific for Lynx1 has been identified (e.g., either a hybridoma-derived monoclonal antibody or a recombinant antibody from a combinatorial library, including monoclonal antibodies to Lynx1 that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest*, Fifth Edition, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker and expressed as a single chain molecule. To inhibit transcription factor activity in a cell, the expression vector encoding the Lynx1-specific intracellular antibody is introduced into the cell by standard transfection methods as described hereinbefore.

iv. Lynx1—Derived Peptidic Compounds

In another embodiment, an inhibitory compound of the invention is a peptidic compound derived from the Lynx1 amino acid sequence (e.g., the sequences disclosed herein as SEQ ID NOs.:1-10). In particular, the inhibitory compound comprises a portion of Lynx1 (or a mimetic thereof) that mediates interaction of Lynx1 with a target molecule such that contact of Lynx1 with this peptidic compound competitively inhibits the interaction of Lynx1 with the target molecule. Exemplary Lynx1 target molecules include neuronal acetylcholine receptors, such as, $\alpha 4\beta 2$ and $\alpha 7$ subunit-containing nicotinic acetycholine receptors.

The peptidic compounds of the invention can be made intracellularly in cells by introducing into the cells an expression vector encoding the peptide. Such expression vectors can be made by standard techniques. The peptide can be expressed intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

Other inhibitory agents that can be used to specifically inhibit the activity of an Lynx1 protein are chemical compounds that directly inhibit Lynx1 activity or inhibit the interaction between Lynx1 and target molecules. Such compounds can be identified using screening assays that select for such compounds, as described in detail below.

B. Stimulatory Agents

In the stimulatory methods of the invention, a moiety which increases the expression and/or activity of Lynx1 may be used. Examples of such stimulatory agents include proteins, nucleic acid molecules, e.g., expression vectors comprising nucleic acid molecules, and chemical agents that stimulate expression and/or activity of Lynx1 in a cell.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A nucleic acid molecule used in the methods of the present invention can be isolated using standard molecular biology techniques. Using all or portion of a nucleic acid sequence of interest as a hybridization probe, nucleic acid molecules can be isolated using standard hybridization and cloning techniques (e.g., as described in Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989).

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived.

A nucleic acid molecule for use in the methods of the invention can also be isolated by the polymerase chain reaction (PCR) using synthetic oligonucleotide primers designed based upon the sequence of a nucleic acid molecule of interest. A nucleic acid molecule used in the methods of the invention can be amplified using cDNA, mRNA or, alternatively, genomic DNA as a template and appropriate oligonucleotide primers according to standard PCR amplification techniques. Furthermore, oligonucleotides corresponding to nucleotide sequences of interest can be prepared by standard synthetic techniques, e.g., using an automated DNA synthesizer.

The nucleic acids for use in the methods of the invention can also be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

A preferred stimulatory agent is a nucleic acid molecule encoding a Lynx1 protein. For example, a cDNA (full length or partial cDNA sequence) is cloned into a recombinant expression vector and the vector is transfected into cells using standard molecular biology techniques. The cDNA can be obtained, for example, by amplification using the polymerase chain reaction (PCR) or by screening an appropriate cDNA library.

Following isolation or amplification of a cDNA, the DNA fragment is introduced into a suitable expression vector. For example, nucleic acid molecules encoding a protein of interest in the form suitable for expression of the protein in a host cell, can be prepared using nucleotide sequences based on the nucleic acid sequence of a nucleic acid molecule encoding the protein of interest.

In one embodiment, a stimulatory agent can be present in an inducible construct. In another embodiment, a stimulatory agent can be present in a construct which leads to constitutive expression.

In one embodiment, the nucleic acid molecules of the invention may be delivered to cells, e.g., neuronal cells, or to subjects using a viral vector, preferably one whose use for gene therapy is well known in the art. Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107(Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401(1996); and Kramm, C. M., et al., Brain Pathology 5:345-381 (1995). Such vectors may be derived from viruses that contain RNA (Vile, R. G., et al., Br. Med Bull. 51:12-30 (1995)) or DNA (Ali M., et al., Gene Ther. 1:367-384 (1994)).

Examples of viral vector systems utilized in the gene therapy art and, thus, suitable for use in the present invention, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J. 11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763,217; Chase, M., et al., Nature Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used in the gene therapy methods of the present invention. Such vectors are described in, for example, Calos, M. P. (1996) *Trends Genet.* 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) *Crit. Rev. Therapeu. Drug Carrier Systems* 12:263-310; Zhang, J., et al. (1996) *Cancer Metastasis Rev.* 15:385-401; Jacoby, D. R., et al. (1997) *Gene Therapy* 4:1281-1283).

In one embodiment, a viral vector for use in the methods of the present invention is an AAV vector. In particular embodiments, the viral vector is an AAV2/5 or AAV2/8 vector. Such vectors are described in, for example, U.S. Pat. No. 7,056, 502, the entire contents of which are incorporated herein by reference.

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan.

Guidance in the construction of gene therapy vectors and the introduction thereof into affected animals for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Generally, methods are known in the art for viral infection of the cells of interest. The virus can be placed in contact with the neuronal cell of interest or alternatively, can be injected into a subject suffering from a disorder associated with neuronal cellular starvation.

The nucleic acid molecules can also be delivered using non-viral methods for gene transfer, preferably those whose use in gene therapy is known in the art (Nakanishi, M., Crit. Rev. Therapeu. Drug Carrier Systems 12:263-310 (1995); Abdallah, B., et al., Biol Cell 85:1-7 (1995); Zhang, J., et al., Cancer Metastasis Rev. 15:385-401 (1996); Philips, S. C., Biologicals 23:13-16 (1995); Lee, R. J. and Huang, L., Crit. Rev. Ther. Drug Carrier Syst. 14:173-206 (1997)). Examples of such non-viral vectors for gene delivery include prokaryotic vectors, cationic liposomes, DNA-protein complexes, non-viral T7 autogene vectors (Chen, X., et al., Hum. Gene Ther. 9:729-736 (1998)), fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburstpolyamidoamine dendrimers (Kukowska-Latallo, J. F., et al., Proc Natl Acad Sci USA 93:4897-4902 (1996); Tang, M. X., et al., Bioconjug. Chem. 7:703-714 (1996)), cationic peptides (Wyman, T. B., et al., Biochemistry 36:3008-3017 (1997)), mammalian artificial chromosomes (Ascenzioni, F., et al., Cancer Lett. 118:135-142 (1997)), and nanoparticles (Parker Read et al. J. Gene Med. 12:86-96 (2010); Frajo et al. PlosOne 1:E38 (2006).

In addition, the present invention provides an embodiment of the foregoing methods wherein the nucleic acid molecules are delivered using any cellular vector, preferably one whose use for gene therapy is well-established for those skilled in the art. Examples of such cellular vectors for gene therapy include endothelial cells (Rancourt, C., et al., Clin. Cancer Res. 4:265-270 (1998); Qjeifo, J. O., et al., Cytokines Mol. Ther. 2:89-101 (1996)) and macrophages including tumor-infiltrating macrophages (Zufferey, R., et al., Nat. Biotechnol. 15:871-875 (1997); Naldini, L., et al., Science 272:263-267 (1996)), each of which may be modified using viral or non-viral vectors to carry the desired nucleic acid molecules, and thus express the desired gene products. Other suitable non-viral vectors will be readily apparent to the skilled artisan.

Gene delivery can be enhanced by including an internal ribosome entry site (IRES) sequence to achieve coordinate expression of multiple genes on a bicistronic message. IRESs are sequences containing 500-600 bp that are typical of the 5' nontransduced regions of picornaviruses, including the polio- and encephalomyocarditis viruses (EMCV). See, e.g., Ghattas, I. R., et al., Molecular and Cellular Biology 11:5848-5859 (1991); Morgan, R. A., et al., Nucleic Acids Research 20:1293-1299 (1992). This approach has been used for efficient retroviral coexpression of the two subunits of interleukin-12 (Tahara, H., et al., J. Immunol. 154:6466-6474

(1995)). Similarly, a viral sequence, the picornavirus 2A sequence, can be used to create mRNAs encoding more than one protein. The viral 2A peptide is 16-20 amino acids and can be employed as a cleavage peptide located between two proteins of interest, where it promotes their cleavage into two separate proteins (Furler et al. Gene Ther. 8:864-873 (2001). Another alternative is for the vector to contain multiple genes under the control of distinct promoters.

IV. Screening Assays

Agents that modulate Lynx1 activity can be known (e.g., Lynx1 interfering nucleic acid molecules, Lynx1 intracellular antibodies that interfere with Lynx1 activity, peptide inhibitors derived from Lynx1) or can be identified using the methods described herein. The invention provides methods (also referred to herein as "screening assays") for identifying other modulators, i.e., candidate or test compounds or agents (e.g., peptidomimetics, small molecules or other drugs) which modulate Lynx1 activity and for testing or optimizing the activity of other agents.

For example, in one embodiment, molecules which bind, e.g., to Lynx1 or a protein interacting with Lynx1, e.g., a nicotinic acetycholine receptor, or have a stimulatory or inhibitory effect on the expression and/or activity of Lynx1 or a protein interacting with Lynx1 can be identified.

In one embodiment, the ability of a compound to directly modulate the expression, post-translational modification, or activity of Lynx1 is measured in an indicator composition using a screening assay of the invention.

Agents that are capable of inhibiting the expression, stability, and/or activity of Lynx1, as identified by the methods of the invention, are useful as candidate compounds useful to increase the neural plasticity of a subject in need thereof or to increase the neural plasticity of a population of neural cells.

For example, in one aspect, the present invention provides methods for identifying a compound useful for treating a subject that would benefit from an increase in neural plasticity. The methods include providing an indicator composition, contacting the indicator composition with a test compound (or a plurality of test compounds), determining the effect of a test compound on the expression and/or activity of Lynx1, and selecting a compound which modulates the expression and/or activity of Lynx1, thereby identifying a compound useful for treating a subject that would benefit from an increase in neural plasticity.

In another aspect, the present invention provides methods for identifying a compound useful for treating a subject that would benefit from an increase in neural plasticity. The methods include administering a test compound (or a plurality of test compounds) to a non-human animal model of neural plasticity, determining the effect of a test compound on the expression and/or activity of Lynx1, and selecting a compound which modulates the expression and/or activity of Lynx1, thereby identifying a compound useful for treating a subject that would benefit from an increase in neural plasticity.

Non-human animal models of neural plasticity, such as learning and memory, animal models of brain damage are known in the art and include, for example, monocular deprivation, surgical esotropia, optically induced concomitant strabismus, and optically induced incomitant strabismus models, sound-rearing, deafening, tactile stimulation, and motor training models.

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carrell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or phage (Scott and Smith (19900 Science 249:386-390; Devlin (1990) Science 249:404-406; Cwirla et al. (1990) Proc. Natl. Acad. Sci. USA 87:6378-6382; and Felici (1991) J. Mol. Biol. 222:301-310), each of which is incorporated herein in its entirety by reference.

The indicator composition can be a cell that expresses the Lynx1 protein or a molecule with which Lynx1 directly interacts, for example, a cell that naturally expresses or has been engineered to express the protein(s) by introducing into the cell an expression vector encoding the protein.

Alternatively, the indicator composition can be a cell-free composition that includes the protein(s) (e.g., a cell extract or a composition that includes e.g., either purified natural or recombinant protein).

Compounds that modulate expression and/or activity of Lynx1, or a non-Lynx1 protein that interacts with Lynx1 can be identified using various "read-outs."

For example, an indicator cell can be transfected with an expression vector, incubated in the presence and in the absence of a test compound, and the effect of the compound on the expression of the molecule or on a biological response regulated by Lynx1 can be determined. The biological activities of Lynx1 include activities determined in vivo, or in vitro, according to standard techniques. Activity can be a direct activity, such as an association with a target molecule or binding partner. Alternatively, the activity is an indirect activity, such as an increase in visual evoked potentials.

To determine whether a test compound modulates Lynx1 protein expression, in vitro transcriptional assays can be performed.

To determine whether a test compound modulates Lynx1 mRNA expression, various methodologies can be performed, such as quantitative or real-time PCR.

A variety of reporter genes are known in the art and are suitable for use in the screening assays of the invention. Examples of suitable reporter genes include those which encode chloramphenicol acetyltransferase, beta-galactosidase, alkaline phosphatase, green fluorescent protein, or luciferase. Standard methods for measuring the activity of these gene products are known in the art.

A variety of cell types are suitable for use as an indicator cell in the screening assay. Preferably a cell line is used which expresses low levels of endogenous Lynx1 and is then engineered to express recombinant protein. Cells for use in the subject assays include eukaryotic cells. For example, in one embodiment, a cell is a fungal cell, such as a yeast cell. In another embodiment, a cell is a plant cell. In yet another embodiment, a cell is a vertebrate cell, e.g., an avian cell or a mammalian cell (e.g., a murine cell, or a human cell).

The cells of the invention can express endogenous Lynx1 or can be engineered to do so. For example, a cell that has been engineered to express the Lynx1 protein can be produced by introducing into the cell an expression vector encoding the protein.

Recombinant expression vectors that can be used for expression of, e.g., Lynx1, are known in the art. For example, the cDNA is first introduced into a recombinant expression vector using standard molecular biology techniques. A cDNA can be obtained, for example, by amplification using the polymerase chain reaction (PCR) or by screening an appropriate cDNA library. The nucleotide sequences of cDNAs for or a molecule in a signal transduction pathway involving (e.g., human, murine and yeast) are known in the art and can be used for the design of PCR primers that allow for amplification of a cDNA by standard PCR methods or for the design of a hybridization probe that can be used to screen a cDNA library using standard hybridization methods.

In another embodiment, the indicator composition is a cell free composition. Lynx1 expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

In one embodiment, compounds that specifically modulate Lynx1 activity or the activity of a molecule in a signal transduction pathway involving Lynx1 are identified based on their ability to modulate the interaction of Lynx1 with a target molecule to which Lynx1 binds. The target molecule can be a mRNA molecule or a protein molecule. Suitable assays are known in the art that allow for the detection of protein-protein interactions (e.g., immunoprecipitations, two-hybrid assays and the like) or that allow for the detection of interactions between Lynx1 and an mRNA (e.g., electrophoretic mobility shift assays, DNAse I footprinting assays and the like). By performing such assays in the presence and absence of test compounds, these assays can be used to identify compounds that modulate (e.g., inhibit or enhance) the activity of Lynx1 with a target molecule.

Compounds identified in the subject screening assays can be used in methods of modulating one or more of the biological responses regulated by Lynx1. It will be understood that it may be desirable to formulate such compound(s) as pharmaceutical compositions (described supra) prior to contacting them with cells.

Once a test compound is identified that directly or indirectly modulates, e.g., Lynx1 expression or activity by one of the variety of methods described hereinbefore, the selected test compound (or "compound of interest") can then be further evaluated for its effect on cells, for example by contacting the compound of interest with cells either in vivo (e.g., by administering the compound of interest to an organis) or ex vivo (e.g., by isolating cells from an organism and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

In another aspect, the invention pertains to a combination of two or more of the assays described herein. For example, a modulating agent can be identified using a cell-based or a cell-free assay, and the ability of the agent to modulate the activity of Lynx1 or a protein with which Lynx1 interacts can be confirmed in vivo, e.g., in an animal, such as, for example, an animal model for, e.g., neural plasticity.

Moreover, a modulator of Lynx1 or a molecule in a signaling pathway involving Lynx1 identified as described herein (e.g., an antisense nucleic acid molecule, or a specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate the activity and/or expression of Lynx1 e.g., by performing screening assays such as those described above using molecules with which Lynx1 interacts, e.g., molecules that act either upstream or downstream of Lynx1 during the critical period of neural plasticity.

The instant invention also pertains to compounds identified in the subject screening assays.

Unless defined otherwise, all technical and scientific terms used herein have the same meaning as commonly understood by one of ordinary skill in the art to which this invention belongs.

It is to be understood that this invention is not limited to particular assay methods, or test agents and experimental conditions described, as such methods and agents may vary. It is also to be understood that the terminology used herein is for the purpose of describing particular embodiments only, and is not intended to be limiting.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Materials and Methods

The following Materials and Methods were used in the examples below.

Animals

Wild-type (C57B1/6; SLC Japan, and Charles River USA) and lynx1 knockout (KO) mice (J. M. Miwa et al., *Neuron*, 51: 587 (2006)) were used. Light-reared (LR) animals were raised from birth on a 12-hour light/dark (L/D) cycle to various postnatal ages. N=3 to 7 mice were used per experimental condition for quantitative Western Blotting or immunohistochemistry.

Lynx1,2 mRNA and β-actin mRNA were quantified by real-time PCR using commercially available gene-specific primers and TaqMan gene expression assay (Applied Biosystems).

Quantitative RT-PCR

In Situ Hybridization

Mouse cDNA fragments of lynx1, lynx2, nAchR β2, PV, or GAD65 were amplified by PCR. Probes were synthesized using T3/T7 RNA polymerase (Roche) labeled with digoxigenin or fluorescein and hybridized to frozen sections. To amplify the signal, probes were detected using anti-digoxigenin or fluorescein antibody conjugated to Alkaline Phosphatase (Roche), or the TSA-Plus DNP System (PerkinElmer Life Sciences) in combination with fast red staining for double FISH.

Western Blotting

Visual cortex from isoflurane-anesthetized mice was dissected and white matter stripped by aspiration before homogenizing by sonication in 50 mM tris-HCl, pH 7.4 containing 10 mM EDTA and 1 mM PMSF. Total protein concentration was determined by colorimetric (Bradford) assay system (BIO RAD) and used to normalize loading. Equal amounts of protein sample (20 or 40 μg per lane) were separated by SDS/PAGE and transferred to PVDF membranes (ATTO Corporation) with semi-dry blotter. Membranes were blocked with 5% skim milk in TBS, pH7.6 containing 0.1% Tween20 for 2 h, then treated with rabbit polyclonal anti-lynx1 (1:1000) (I. Ibanez-Tallon et al., Neuron, 33: 893 (2002)) overnight at 4° C., washed and incubated with AP-conjugated secondary antibody. Blots were visualized by adding NBT/BCIP solution.

Immunohistochemistry

Mice were perfused transcardially with 0.9% saline then 4% paraformaldehyde, and brains removed into 30% sucrose/paraformaldehyde for cryoprotection. Brains were cut in coronal section (30 μm) on a freezing microtome. Sections were rinsed in PBS, then incubated overnight at 4° C. in monoclonal antibody against Myelin Basic Protein (MBP: Chemicon, 1:200) or biotin-WFA (1:400), followed by secondary antibodies (anti-mouse IgG-Alexa-488, 594, streptavidin-488, 1:400).

Monocular Deprivation (MD) Procedure

Eyelid margins were trimmed by iris scissor and eyes sutured shut under isoflurane anesthesia. Eyes were closed 4-5 days for short term MD (STMD), from P19 to >P60 for long term MD (CP-LTMD), and from P19 to P33 for recovery studies.

Extracellular Recording In Vivo

Electrophysiological recording was performed under nembutal/chlorprothixene anesthesia using standard techniques for mice (T. K. Hensch et al., Science 282: 1504 (1998); J. A. Gordon, M. P. Stryker, J Neurosci 16: 3274 (1996). Ocular dominance in the binocular zone of each mouse was calculated as a contralateral bias index (CBI): [(n1−n7)+2/3(n2−n6)+1/3(n3−n5)+N]/2N, where N=total number of cells and nx=number of cells corresponding to ocular dominance score of x (J. A. Gordon, M. P. Stryker, J Neurosci 16, 3274 (1996)). For statistical comparison of OD distributions, normalized OD scores of single neurons were plotted as cumulative distribution for each experimental group. OD score was computed by PSTH analysis of peak to baseline spiking activity in response to each eye: {[Peak(ipsi)−baseline(ipsi)]−[Peak(contra)-baseline(contra)]}/{[Peak(ipsi)-baseline(ipsi)]+[Peak(contra)-baseline(contra)]}(T. Pizzorusso et al., Science, 298: 1248 (2002)).

Visual Evoked Potentials

VEPs were recorded under nembutal/chlorprothixene anesthesia using standard techniques in mice (V. Porciatti, T. Pizzorusso, L. Maffei, Vision Res, 39: 3071 (1999)). A tungsten electrode was inserted into V1 where the maximal VEP response is located within the visual field 20° from the vertical meridian (usually 3 mm from lambda). To record VEPs, the electrode was advanced to a depth of 100-400 μm within cortex where VEPs exhibit their maximal amplitude. Signals were band-pass-filtered (0.1-100 Hz), amplified, and fed to a computer for analysis. In brief, at least 20 events were averaged in synchrony with the stimulus contrast reversal. Transient VEPs in response to abrupt contrast reversal (1 Hz) were evaluated in the time domain by measuring the peak-to-baseline amplitude of the major negative component. Visual stimuli were horizontal sinusoidal gratings of different spatial frequencies at 90% contrast. Visual acuity was obtained by extrapolation to zero amplitude of the linear regression through the last four to five data points along a curve of VEP amplitude plotted against log spatial frequency.

Drug Administration

Nicotine (1 mg/kg, s.c.) was injected during VEP recording from V1. Mecamylamine (2.5 mg/kg) or a mixture of α4-+α7-selective DHβE (2 mg/kg)+MLA (5 mg/kg) were administered systemically (daily, i.p.) (J. A. Davis, T. J. Gould, Psychopharmacol., 184: 345 (2006)). Focal mecamylamine (50 mM) or Diazepam (2 mg/ml in 50% propylene glycol) were administered via low-flow osmotic mini-pump infusion directly into V1 (1.0 μl/hr, 200 ml over 5-7 days; Alzet Model 2001, Alza) before recording (T. K. Hensch et al., Science 282, 1504 (1998)). Acetylcholinesterase Inhibitor (AchEI: physostigmine, 0.1 mg/kg, i.p.) was injected daily from P45 until one day before recording.

Example 1

Lynx1, a Cholinergic Brake, Limits Plasticity in Adult Visual Cortex

Figure 2:
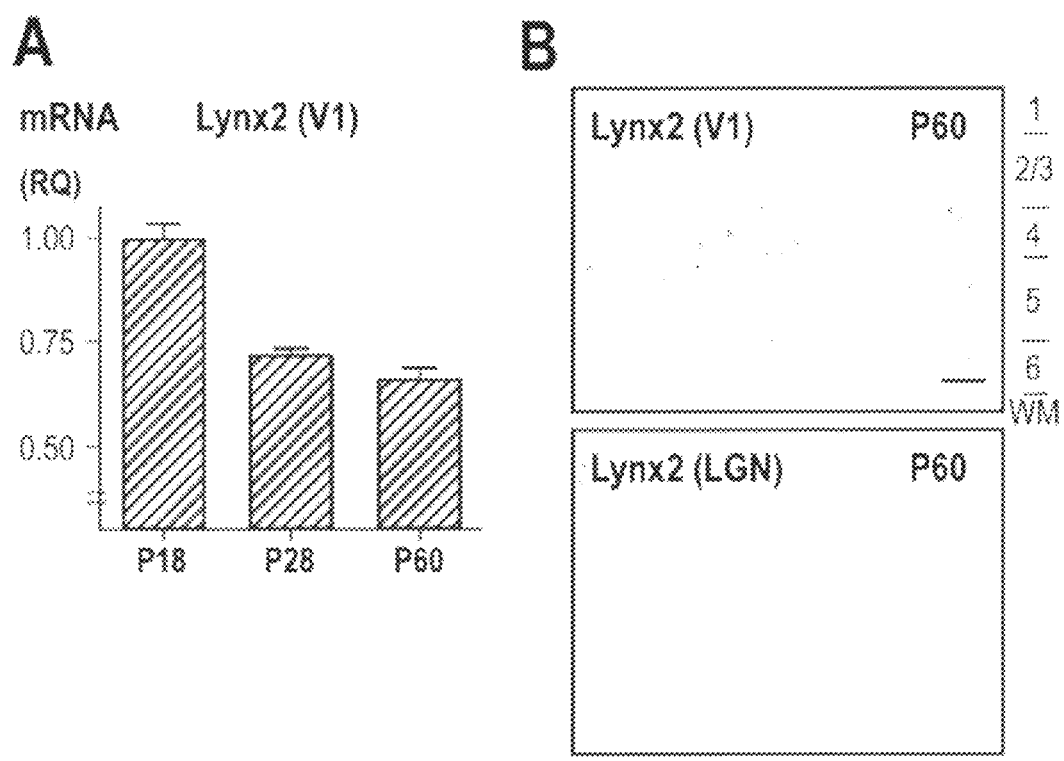
FIGS. 2A-2C depict Lynx2 expression in the visual system. (A) Lynx2 mRNA expression decreases across CP. $P<0.0001$, One-way ANOVA. Mean±sem. (B) In situ hybridization of lynx2 in adult V1 (upper panel) and LGN (lower panel). Scale, 100 μm (C) Double in situ hybridization of lynx2 (whte) & PV (gray) in adult V1. Note lynx2 does not co-localize with PV, while lynx1 does (FIG. 4B).
Figure 2:
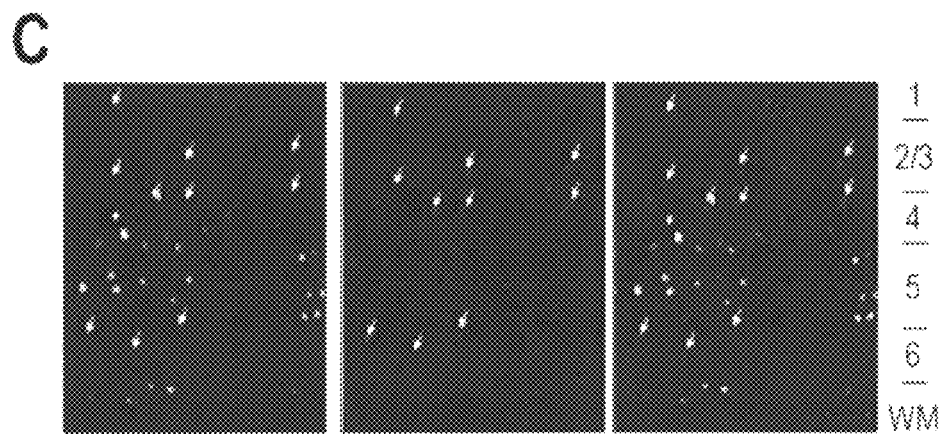

In order to identify molecules responsible for the gradual emergence of molecular "brakes" that actively prevent plasticity in the adult brain, the transcriptome of the binocular zone in mouse V1 was analysed for molecules that are expressed more in adulthood than during the critical period (Plessy et al., PLoS ONE 3, e3012 (2008)). Lynx1 was identified as one such molecule. Lynx1 is an endogenous prototoxin similar to a-bungarotoxin in snake venom and binds to the nicotinic acetylcholine receptor (nAChR) (J. M. Miwa et al., Neuron 23, 105 (1999). Lynx1 expression increases only after the critical period for amblyopia in adult V1 both at the protein and mRNA level (FIG. 1A). Along the visual pathway, Lynx1 transcripts were expressed both in V1 and the lateral geniculate nucleus (LGN) (FIG. 1B). In contrast, expression of another member of the lynx family, Lynx2, declined over the critical period and was hardly found in the visual pathway (FIG. 2).

Figure 3:
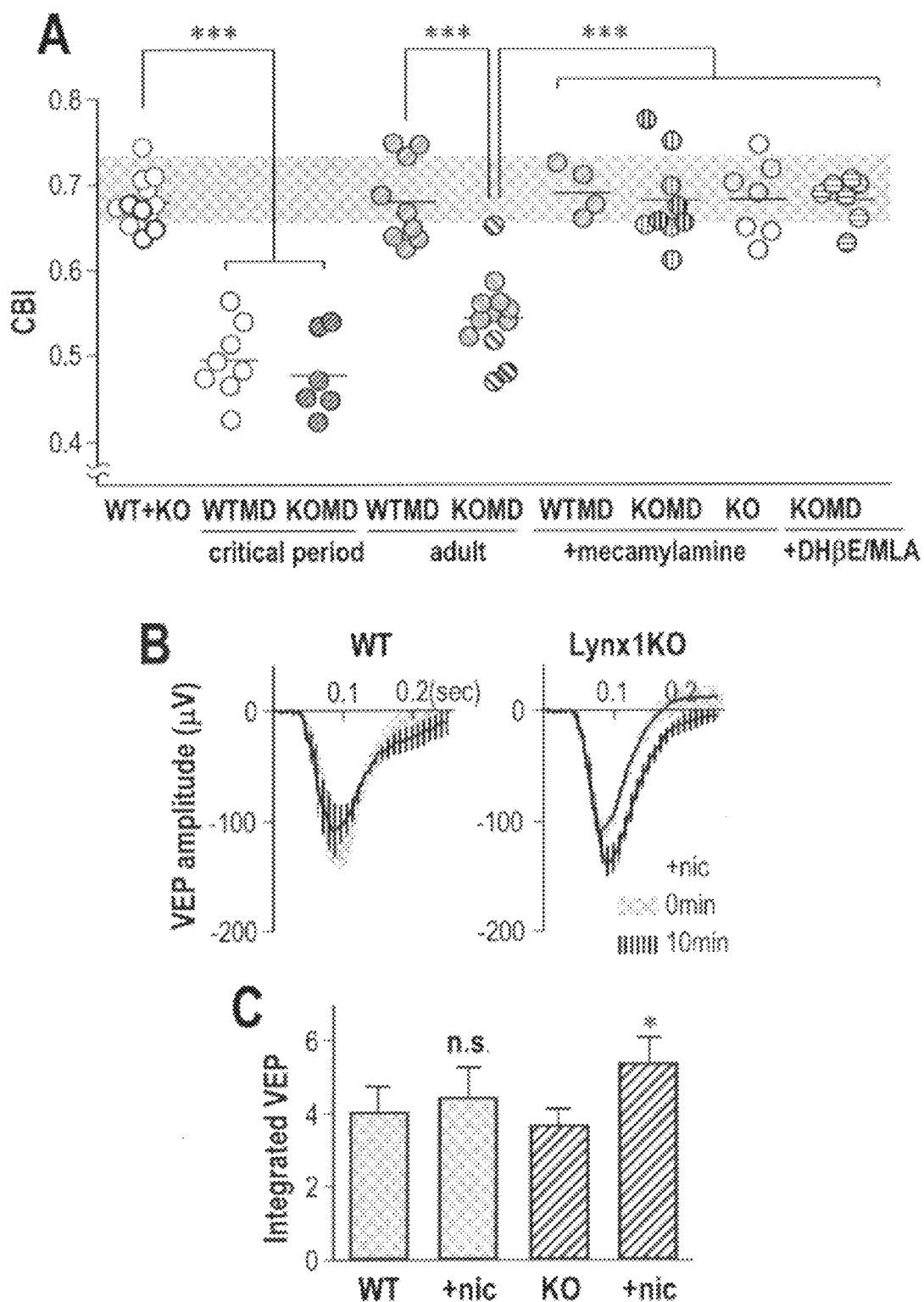
FIGS. 3A-3C depict nicotinic receptors mediate adult plasticity in Lynx1 KO mice. (A) Mice without MD shift equally after MD during the CP (light blue, KO: mean CBI=0.48, 6 mice; light gray, WT: CBI=0.50, 8 mice; $P>0.5$, t test). Adult plasticity (KOMD: CBI=0.55, 12 mice versus gray, WTMD: CBI=0.68, 9 mice; $*P<0.0001$, t test) is abolished by concurrent nAChR antagonists (KOMD+mecamylamine: CBI=0.68, 9 mice versus KOMD, $*P<0.0001$; versus gray, WTMD+mecamylamine: CBI=0.69, 4 mice, $P>0.7$; versus no MDKO+mecamylamine: CBI=0.68, 7 mice, $P>0.9$, t test; KOMD+DHβE/MLA: CBI=0.68, 7 mice versus KOMD, $***P<0.0001$, t test). Darker circles represent cortical minipump infusion. (B) Enhanced nicotine response in Lynx1 KO mice. Averaged VEP traces (mean T SEM) before (light gray) and 10 min after (black) subcutaneous nicotine injection (+nic) in WT (left) and Lynx1 KO mice (right). (C) Integrated VEP (area of first negative peak) for WT (empty bars, 6 mice) and Lynx1 KO mice (filled bars, 11 mice). $*P<0.05$, t test; n.s., not significant.

Lynx1 function in the binocular region was therefore directly assessed by electrophysiological recordings from knockout mice. In mice lacking the Lynx1 gene, the eye preference of single neurons (ocular dominance) was no different from that of wild-type mice (FIG. 1E). Upon short-term (4 day) monocular deprivation (MD) in mature wild-type animals (>postnatal day 60, P60), there was little change in the visual spiking response (H. Morishita, T. K. Hensch, Curr. Opin. Neurobiol. 18, 101 (2008). Instead, adult Lynx1 knockout mice exhibited a robust shift in responsiveness away from the deprived eye (FIG. 1, C to E). This heightened plasticity was specific to older ages, because short-term MD was equally effective in both wild-type and Lynx1 knockout mice during the critical period (FIG. 3A). Lynx1 protein directly binds to nAChRs (I. Ibañez-Tallon et al., Neuron 33, 893 (2002)), such as the major central subunits $α_4β_2$ heteromers or $α_7$ homomers, to reduce their sensitivity to acetylcholine. The response to systemic nicotine injection in Lynx1 knockout mice was directly assessed by measuring visual evoked potential (VEP) response in anesthetized V1. Enhancement of the VEP response was only observed in Lynx1 knockout mice (FIGS. 3, B and C). To test whether nAChR signaling mediates adult plasticity in Lynx1 knockout mice, the broadspectrum antagonist mecamylamine was applied concurrent with short-term MD. Either systemic injection or restricted infusion directly into V1 by osmotic minipump was sufficient to prevent adult plasticity. These results were corroborated by systemic treatment with a mixture of $\alpha_4$- and $\alpha_7$-subunit—selective nAChR antagonists (J. A. Davis, T. J. Gould, *Psychopharmacology* (Berl.) 184, 345 (2006)), dihydro-$\beta$-erythroidine (DH$\beta$E) plus methyllycaconitine (MLA) (FIG. 3A).

Figure 4:
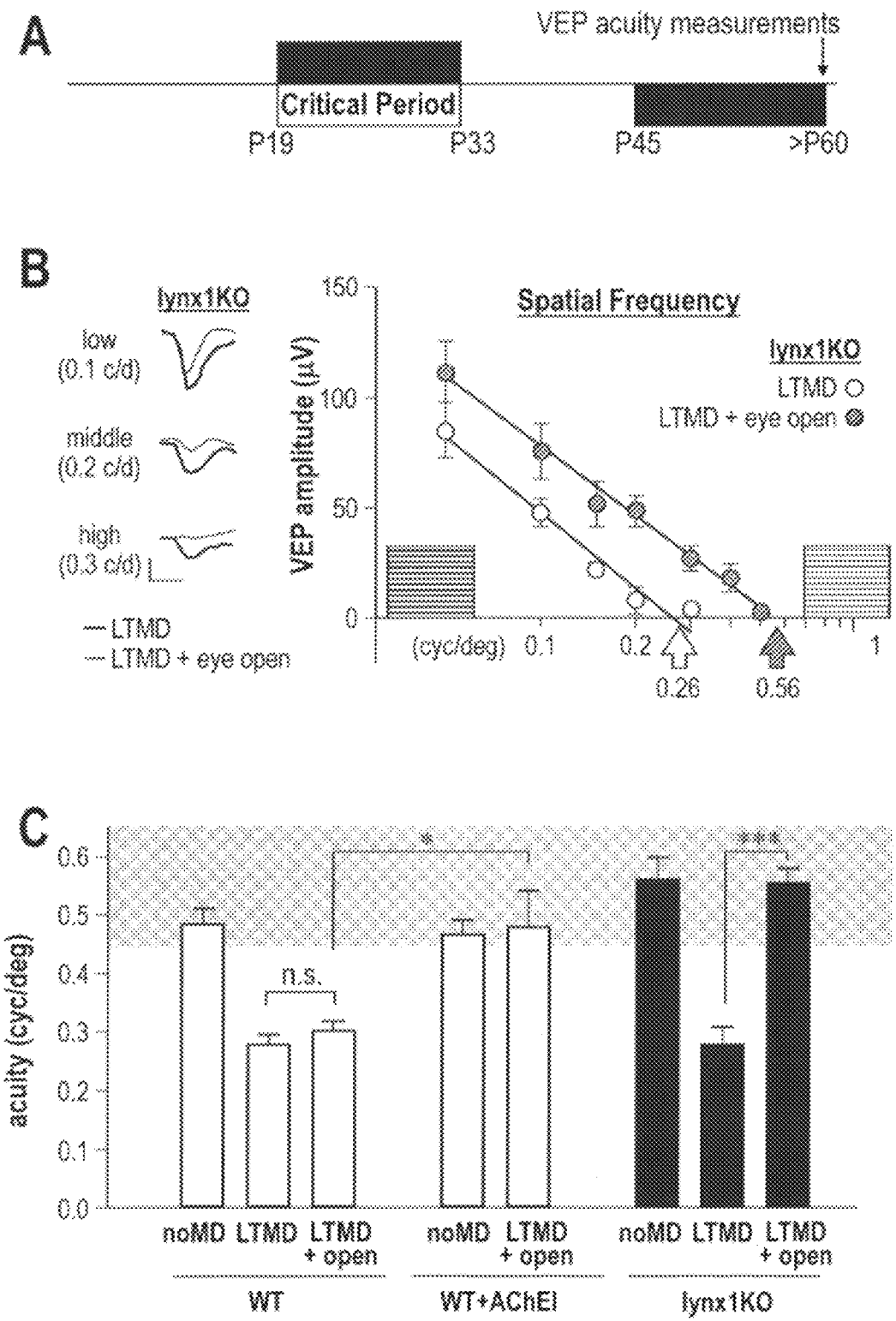
FIGS. 4A-4C depict the recovery from amblyopia in Lynx1 KO mice. (A) After long-term MD (LTMD) spanning the critical period (P19 to P33), the deprived eye was reopened (>1 month) until VEP acuity was measured in V1 (>P60). For AChEI experiments, physostigmine was injected daily starting at P45. (B) Averaged VEP traces (left, mean±SEM; scale: 20 mV, 0.1 s) and amplitudes (right) of first negative peak (mean±SEM) reveal acuity recovery after reopening an eye (dark gray, 6 mice) initially deprived during the critical period (light gray, 5 mice). (C) Visual acuity in WT mice (white bars) without deprivation [no MD: 0.48 T 0.03 cycles per degree (cyc/deg), 6 mice] decreases after LTMD spanning the critical period (LTMD: 0.28±0.01 cyc/deg, 3 mice) and endures (+eye open: 0.30 T 0.02 cyc/deg, 5 mice; versus LTMD, $P>0.45$; versus no MD, $P<0.0005$, t test). In contrast, reopening the deprived eye together with cholinesterase inhibitor restores vision (gray bar, AChEI: 0.48±0.06 cyc/deg, 4 mice; versus WT+eye open, $*P<0.05$; versus WT no MD+AChEI: 0.47±0.02 cyc/deg, 6 mice, $P>0.8$, t test). Lynx1 KO mice (black bars) spontaneously recover from LTMD (0.28±0.03 cyc/deg, 5 mice) simply by reopening the deprived eye (0.56±0.02 cyc/deg, 6 mice; $***P<0.0001$, t test) to reach normal levels (no MD: 0.56±0.04 cyc/deg, 3 mice).

To establish the clinical relevance of these findings, recovery from amblyopia was directly measured in adulthood. In wild-type mice, long-term MD spanning the entire critical period results in a significant reduction of visual acuity as measured directly in V1 by VEP (H. Morishita, T. K. Hensch, *Curr. Opin. Neurobiol.* 18, 101 (2008)). Notably, this reduction persisted into adulthood even if the closed eye was reopened for more than 1 month after the critical period (FIGS. 4, A and C). Lynx1 knockout mice spontaneously recovered visual acuity to normal levels simply by reopening the closed eye (FIGS. 4, A and C), exhibiting VEPs even at higher spatial frequencies (FIG. 4B). Given the cholinergic basis of this plasticity, attempts to induce recovery even in adult wild-type mice by enhancing endogenous ACh signaling were performed. Injection of an acetylcholinesterase inhibitor, physostigmine, during the period of eye reopening similarly restored vision to wild-type mice initially rendered amblyopic (FIG. 4C).

Figure 5:
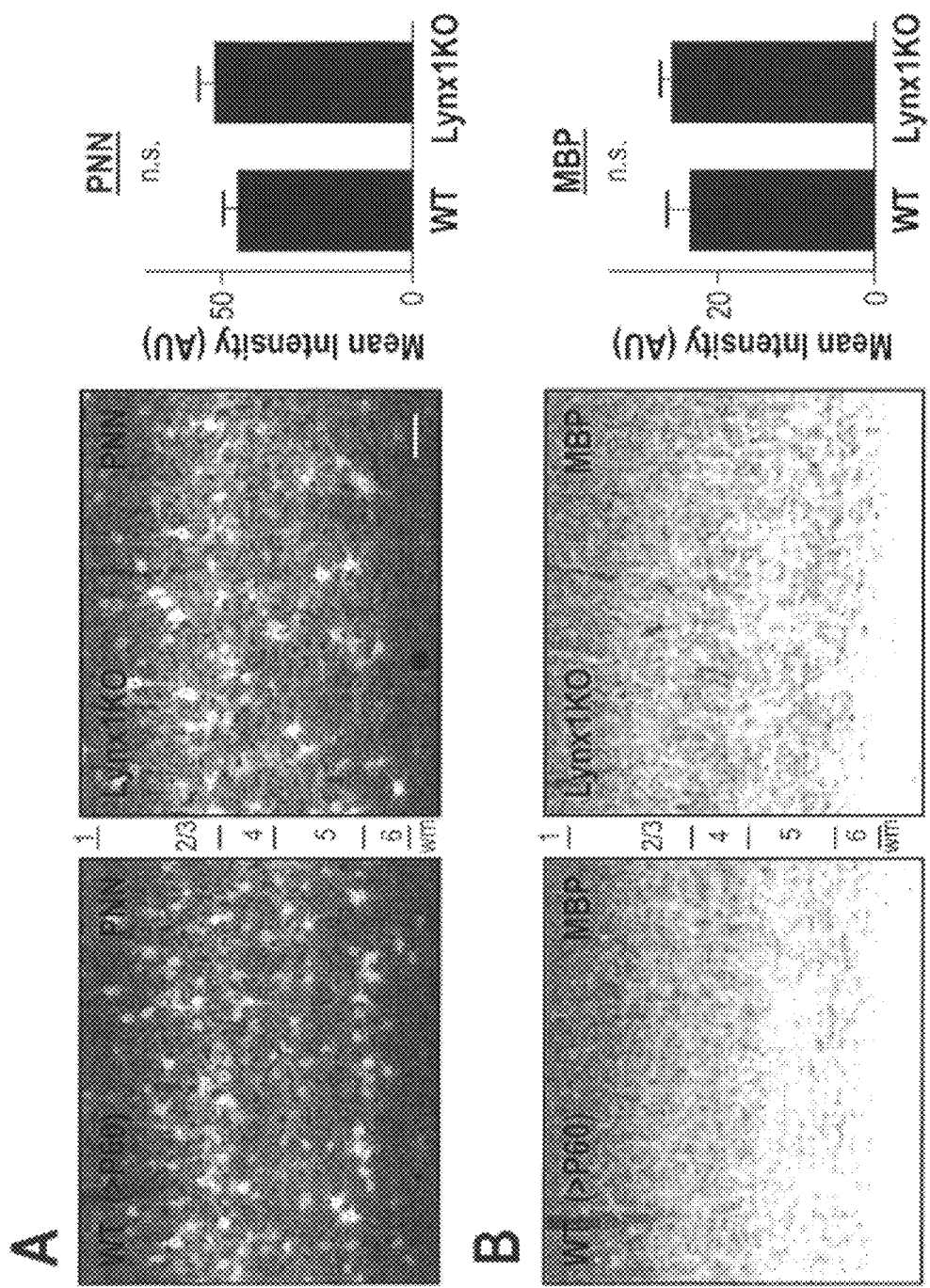
FIGS. 5A-5B depict normal perineuronal nets and myelination in Lynx1 KO mice. (A) WFA staining of adult V1 in WT (left) and lynx1 KO (middle) mice. $P>0.3$, t-test. (B) MBP staining of adult V1 in WT (left) and lynx1 KO (middle) mice. $P>0.4$, t-test. Scale, 100 μm.
Figure 6:
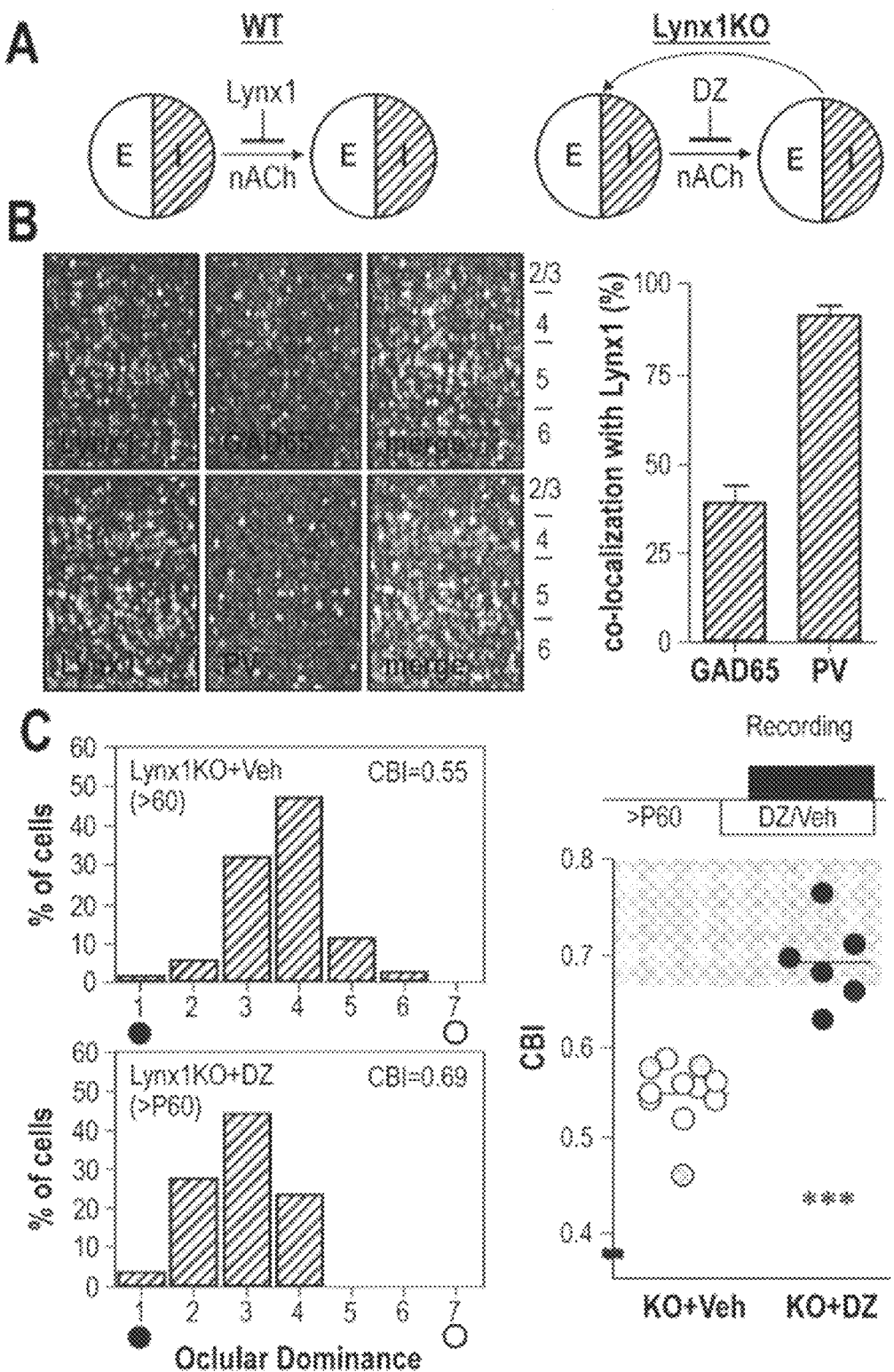
FIGS. 6A-6C depict that Lynx1 adjusts cortical excitatory-inhibitory balance to regulate adult plasticity. (A) In WT animals (left), mature excitatory-inhibitory balance is maintained by Lynx1 that limits nAChR response. In Lynx1 KO mice (right), enhanced nAChR signaling leads to excitatory-inhibitory imbalance and adult plasticity, which could be sensitive to acute restoration of inhibition with diazepam (DZ). (B) Double in situ hybridization of Lynx1 (white) with GAD65 (light gray, top) or parvalbumin (PV, bottom) in adult V1 (left). Scale bar, 100 μm. Quantification of overlapping pixels (right) indicates selective expression of Lynx1 in a subset (40%) of GAD65-positive interneurons, most likely PV-positive cells (>90% colocalization). (C) Focal diazepam infusion during adult MD in Lynx1 KO mice abolishes ocular dominance plasticity (black, DZ: CBI=0.67, 6 mice versus gray, vehicle (Veh): CBI=0.54, 14 mice; $***P<0.001$, t test). Dark circles represent cortical minipump infusion.

Recovery of function in Lynx1 knockout mice is likely due to an enhanced visual responsiveness during arousal. Structural changes at the level of perineuronal nets (T. Pizzorusso et al., *Science* 298, 1248 (2002)) or myelination (A. W. McGee, Y et al., *Science* 309, 2222 (2005)) in Lynx1 knockout mice (FIG. 5) were not observed. Aging-related neurodegeneration reported previously in these animals (J. M. Miwa et al., *Neuron* 51, 587 (2006)) was confirmed to occur only past 9 months of age. Instead, local excitatory-inhibitory circuit balance might have been affected earlier (H. Morishita, T. K. Hensch, *Curr. Opin. Neurobiol.* 18, 101 (2008)) (FIG. 6A). Previous reports across various species have localized nAChRs to thalamocortical terminals presynaptic to principal cells (A. A. Disney, C. Aoki, M. J. Hawken, *Neuron* 56, 701 (2007); G. T. Prusky, C. Shaw, M. S. Cynader, *Brain Res.* 412, 131 (1987); D. Parkinson, K. E. Kratz, N. W. Daw, *Exp. Brain Res.* 73, 553 (1988); Z. Gil, B. W. Connors, Y. Amitai, *Neuron* 19, 679 (1997); I. Kruglikov, B. Rudy, *Neuron* 58, 911 (2008)), facilitating excitation in V1 (E. Lucas-Meunier et al., *Cereb. Cortex* 19, 2411 (2009); M. C. Kuo, D. D. Rasmusson, H. C. Dringenberg, *Neuroscience* 163, 430 (2009)). Activation of nAChRs upon specific inhibitory neurons could further modulate excitatoryinhibitory balance by disinhibition (P. Aracri et al., Cereb. *Cortex* 20, 1539 (2010); M. Alkondon, et al. *J. Neurosci.* 20, 66 (2000)), as in the case of congenital nAChR mutation that disrupts GABA-mediated transmission (E. O. Mann, I. Mody, *Curr. Opin. Neurol.* 21, 155 (2008)).

Figure 7:
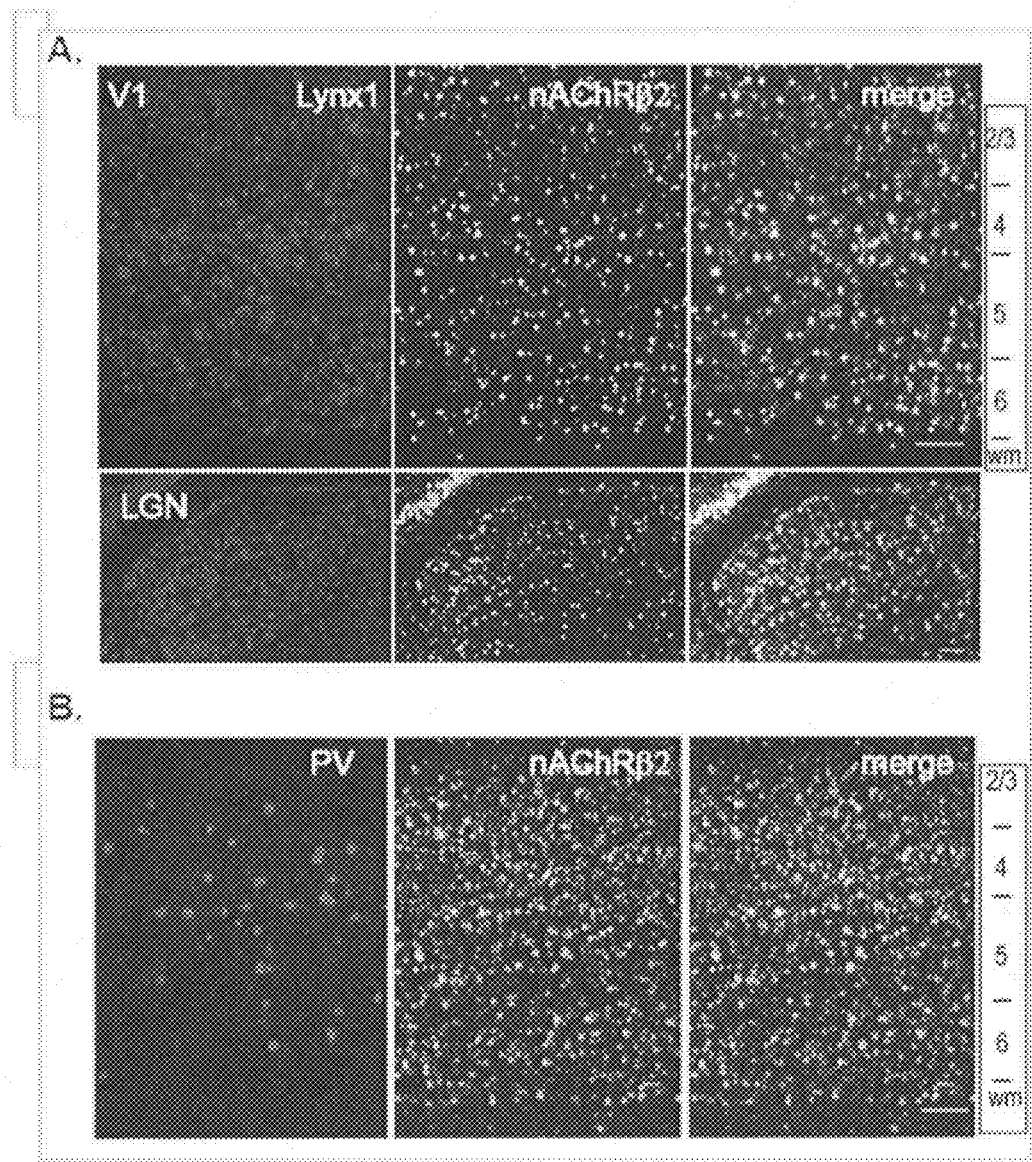
FIGS. 7A-7B depict co-localization of nAchR β2 subunit with lynx1 and PV in the visual system. (A) Double in situ hybridization of lynx1 (dark gray) and nAChR β2 (white) in adult V1 and LGN. Scale, 100 μm (B) Double in situ hybridization of PV (dark gray) and nAChR β2 (white) in adult V 1. Scale, 100 μm

Indeed, Lynx1 and nAChR mRNAs were coexpressed not only in the LGN (FIG. 7) but also in a subpopulation of GABA cells, primarily parvalbumin-positive interneurons (FIG. 6B and FIG. 7B). Activation of nAChRs may also exert long-term epigenetic effects on GABA synthesis R. Satta et al., *Proc. Natl. Acad. Sci. U.S.A.* 105, 16356 (2008)). To probe whether excitatory-inhibitory imbalance may contribute to adult plasticity in Lynx1 knockout mice, intracortical inhibition was directly restored by focal benzodiazepine infusion from osmotic minipumps. Diazepam treatment of V1 abolished adult plasticity in Lynx1 knockout mice (FIG. 6C), as did nAChR blockade (FIG. 3A). Thus, Lynx1 reduces adult plasticity through cholinergic signaling mechanisms that may adjust excitatoryinhibitory balance later in life (H. Morishita, T. K. Hensch, *Curr. Opin. Neurobiol.* 18, 101 (2008)).

Taken together, Lynx1 provides both a valuable endogenous tool with which to probe critical period closure and offers novel therapeutic and conceptual insight. In contrast to muscarinic receptors engaged during the critical period (Q. Gu, W. Singer, *Eur. J. Neurosci.* 5, 475 (1993)), the results presented herein highlight a nicotinic component for adult V1 plasticity. Although a role for muscarinic receptors is not ruled out (J. L. Herrero et al., *Nature* 454, 1110 (2008)), deletion of Lynx1 alone is sufficient to rescue visual acuity. Recovery strategies aimed at the Lynx1-nAChR interaction (J. M. Miwa et al., *Neuron* 23, 105 (1999); I. Ibañez-Tallon et al., *Neuron* 33, 893 (2002).) could be fruitful in conjunction with attentional tasks that stimulate cholinergic release (e.g., perceptual learning, video-game training) (M. Goard, Y. Dan, *Nat. Neurosci.* 12, 1444 (2009); J. I. Kang, E. Vaucher, *PLoS ONE* 4, e5995 (2009); D. M. Levi, R. W. Li, *Philos. Trans. R. Soc. Lond. B Biol. Sci.* 364, 399 (2009); M. W. Dye, C. S. Green, D. Bavelier, *Neuropsychologia* 47, 1780 (2009)). Clinically approved cholinesterase inhibitors that boost the afferent response in human visual cortex (M. A. Silver, A. Shenhav, M. D'Esposito, *Neuron* 60, 904 (2008)) may be useful for treating some amblyopes (FIG. 3C), including those with subcortical changes (R. F. Hess, B. Thompson, G. Gole, K. T. Mullen, *Eur. J. Neurosci.* 29, 1064 (2009)). Amblyopia might further serve as a diagnostic measure to identify tobacco exposure (P. Lempert, *Ophthalmic Physiol. Opt.* 25, 592 (2005)) or schizophrenia (M. Suter, et al. *Brain Res. Brain Res. Rev.* 48, 98 (2005).).

Although a permissive role for cholinergic input has long been appreciated during the critical period (M. F. Bear, W. Singer, *Nature* 320, 172 (1986)), it has remained a mystery why V1 plasticity is severely restricted in adulthood even in the presence of massive innervation from the basal forebrain. Lynx1 expression not only contributes to nAChR agonist binding and desensitization kinetics (J. M. Miwa et al., *Neuron* 23, 105 (1999)), but also may respond to changes in network activity (C. K. Pfeffer et al., *J. Neurosci.* 29, 3419 (2009)). Local regulation of Lynx1 levels may allow cholinergic activation to induce islands of plasticity while maintaining overall circuit stability. Visual attention tasks in fact preferentially modulate fastspiking inhibitory neurons (J. F. Mitchell, et al., *Neuron* 55, 131 (2007); Y. Chen et al., *Nat. Neurosci.* 11, 974 (2008)), consistent with a convergence of top-down influences upon local excitatory-inhibitory circuit balance.

EQUIVALENTS

Those skilled in the art will recognize, or be able to ascertain using no more that routine experimentation, many equivalents to the specific embodiments of the invention described herein. Such equivalents are intended to be encompassed by the following claims.

What is claimed is:

1. A method for treating an 8- to 17-year-old human subject having amblyopia, the method comprising orally administering a therapeutically effective amount of donepezil to an 8- to 17-year-old human subject having amblyopia, thereby treating the subject.

2. A method for treating an 8- to 17-year-old human subject having amblyopia, the method comprising orally administering a therapeutically effective amount of galantamine to an 8- to 17-year-old human subject having amblyopia, thereby treating the subject.

3. The method of claim 1 or 2, further comprising administering to said subject an additional cholinesterase inhibitor.

4. The method of claim 1 or 2, wherein the administering results in a decrease in the levels or an activity of Lynx 1 in the subject.

5. A method for increasing the plasticity of a primary visual cortex in an 8- to 17-year-old human subject having amblyopia, the method comprising: orally administering to an 8- to 17-year-old human subject having amblyopia an amount of donepezil sufficient to decrease the levels or an activity of Lynx1 in the subject, thereby increasing the plasticity of the primary visual cortex in the subject.

6. A method for increasing the plasticity of a primary visual cortex in an 8- to 17-year-old human subject having amblyopia, the method comprising: orally administering to an 8- to 17-year-old human subject having amblyopia an amount of galantamine sufficient to decrease the levels or an activity of Lynx1 in the subject, thereby increasing the plasticity of the primary visual cortex in the subject.

7. The method of claim 1, wherein the subject is 10 to 15 years old.

8. The method of claim 1, wherein the subject is administered about 2.5 mg donepezil per day.

9. The method of claim 1, further comprising patching of an unaffected eye of the subject.

10. The method of claim 4, wherein the activity of Lynx1 is the ability of Lynx1 to bind to a nicotinic acetylcholine receptor or reduce nicotinic acetylcholine receptor sensitivity to acetylcholine.

11. The method of claim 2, wherein the subject is 10 to 15 years old.

12. The method of claim 2, further comprising patching of an unaffected eye of the subject.

13. The method of claim 5, wherein the subject is administered about 2.5 mg donepezil per day.

14. The method of claim 6, wherein the galantamine is administered daily.

15. The method of claim 6, wherein the subject is 10 to 15 years old.

* * * * *

UNITED STATES PATENT AND TRADEMARK OFFICE
CERTIFICATE OF CORRECTION

PATENT NO. : 9,345,696 B2
APPLICATION NO. : 13/294490
DATED : May 24, 2016
INVENTOR(S) : Takao K. Hensch Page 1 of 1

It is certified that error appears in the above-identified patent and that said Letters Patent is hereby corrected as shown below:

In the Claims

Col. 53, line 44, Claim 4, delete "Lynx 1" and insert -- Lynx1 --, therefor.

Signed and Sealed this
Ninth Day of August, 2016

Michelle K. Lee
*Director of the United States Patent and Trademark Office*

SEQUENCE LISTING

<160> NUMBER OF SEQ ID NOS: 10

<210> SEQ ID NO 1
<211> LENGTH: 131
<212> TYPE: PRT
<213> ORGANISM: Homo sapiens

<400> SEQUENCE: 1

Met Thr Pro Leu Leu Thr Leu Ile Leu Val Val Leu Met Gly Leu Pro
1               5                   10                  15

Leu Ala Gln Ala Leu Asp Cys His Val Cys Ala Tyr Asn Gly Asp Asn
            20                  25                  30

Cys Phe Asn Pro Met Arg Cys Pro Ala Met Val Ala Tyr Cys Met Thr
        35                  40                  45

Thr Arg Thr Ser Ala Ala Glu Ala Ile Trp Cys His Gln Cys Thr Gly
    50                  55                  60

Phe Gly Gly Cys Ser His Gly Ser Arg Cys Leu Arg Asp Ser Thr His
65                  70                  75                  80

Cys Val Thr Thr Ala Thr Arg Val Leu Ser Asn Thr Glu Asp Leu Pro
                85                  90                  95

Leu Val Thr Lys Met Cys His Ile Gly Cys Pro Asp Ile Pro Ser Leu
            100                 105                 110

Gly Leu Gly Pro Tyr Val Ser Ile Ala Cys Cys Gln Thr Ser Leu Cys
        115                 120                 125

Asn His Asp
    130

<210> SEQ ID NO 2
<211> LENGTH: 1290
<212> TYPE: DNA
<213> ORGANISM: Homo sapiens

<400> SEQUENCE: 2
ttagggtaga agaaaaggtt ttattttct ttctcacatt ggaaaaaatg aaaactttcg      60
gacccatgaa attttattac attttgccaa aaacagaacc aataacataa gtattcaaag    120
ttatgtaaag ataattattt aatatgaaca ttatgatggt gagagggacc acggagcaag    180
gggctgcctt gcaggcctgc cttccagctt tgctacaggg accagaagcg ggagctgagc    240 gcagggagg caggcggagg ccatgggcag cgaggcgggt gcgccaaagg gcgccagttc     300
cggagctgct gggcctgggc tgcaggaggg cggagctggg gccgcaaggc tggtgccggc    360
cgacaaacga cgcggcgcgg gcgagtgggc ggaggcggct gcggggaagg ctgggctgcc    420
gcgggacgcg gtgaagatag cctgcggagt gtccgggctg aacacggttg cagcactccc    480
agtagaccag gagctccggg aggcagggcc ggccccacgt cctctgcgca ccaccctgag    540
ttggatcctc tgtgcgccac ctgagttgga tccaggcta gctgctgttg acctccccac     600
tcccacgctg ccctcctgcc tgcagccatg acgcccctgc tcaccctgat cctggtggtc    660
ctcatgggct tacctctggc ccaggccttg gactgccacg tgtgtgccta acaacggagac    720 aactgcttca accccatgcg ctgcccggct atggttgcct actgcatgac cacgcgcacc    780
tctgcagccg aagccatatg gtgtcaccag tgcacgggct cggagggtg ctcccatgga     840 tccagatgcc tgagggactc cacccactgt gtcaccactg cccacccggt cctcagcaac    900
accgaggatt tgcctctggt caccaagatg tgccacatag ctgccccga tatcccagc      960 ctgggcctgg gccccatacgt atccatcgct tgctgccaga ccagcctctg caaccatgac  1020

```
tgacggctgc cctcctccag gccccggac gctcagcccc acagccccc acagcctggc    1080 gccagggctc acagctgccc ctccctcgag actggccagc ccacctctcc cggcctctgc    1140
agccaccgtc cagcaccgct tgtcctaggg aagtcctgcg tggagtcttg cctcaatctg    1200
ctgccgtcca agcctggggc ccatcgtgcc tgccgcccct tcaggtcccg acctccccac    1260
aataaaatgt gattggatcg tgtggtacaa                                     1290
```

```
<210> SEQ ID NO 3
<211> LENGTH: 116
<212> TYPE: PRT
<213> ORGANISM: Homo sapiens

<400> SEQUENCE: 3

Met Thr Pro Leu Leu Thr Leu Ile Leu Val Val Leu Met Gly Leu Pro
  1               5                  10                  15

Leu Ala Gln Ala Leu Asp Cys His Val Cys Ala Tyr Asn Gly Asp Asn
             20                  25                  30

Cys Phe Asn Pro Met Arg Cys Pro Ala Met Val Ala Tyr Cys Met Thr
         35                  40                  45

Thr Arg Thr Tyr Tyr Thr Pro Thr Arg Met Lys Val Ser Lys Ser Cys
 50                  55                  60

Val Pro Arg Cys Phe Glu Thr Val Tyr Asp Gly Tyr Ser Lys His Ala
 65                  70                  75                  80

Ser Thr Thr Ser Cys Cys Gln Tyr Asp Leu Cys Asn Gly Thr Gly Leu
                 85                  90                  95

Ala Thr Pro Ala Thr Leu Ala Leu Ala Pro Ile Leu Leu Ala Thr Leu
            100                 105                 110

Trp Gly Leu Leu
        115
```

```
<210> SEQ ID NO 4
<211> LENGTH: 4967
<212> TYPE: DNA
<213> ORGANISM: Homo sapiens

<400> SEQUENCE: 4
tttagggtag aagaaaaggt tttatttttc tttctcacat tggaaaaaat gaaaactttc      60
ggacccatga aattttatta cattttgcca aaaacagaac caataacata agtattcaaa     120
gttatgtaaa gataattatt taatatgaac attatgatgg tgagagggac cacggagcaa     180
ggggctgcct tgcaggcctg ccttccagct ttgctacagg gaccagaagc gggagctgag     240
cgcaggggag gcaggcggag gccatgggca gcgaggcggg tgcgccaaag gcgccagtt      300 ccggagctgc tgggcctggg ctgcaggagg gcggagctgg ggccgcaagg ctggtgccgg     360
ccgacaaacg acgcggcgcg ggcgagtggg cggaggcggc tgcggggaag gctgggctgc     420
cgcgggacgc ggtgaagata gcctgcgag tgtccgggct gaacacggtt gcagcactcc     480
cagtagacca ggagctccgg gaggcagggc cggcccacg tcctctgcgc accaccctga     540
gttggatcct ctgtgcgcca cctgagttgg atccagggct agctgctgtt gacctcccca     600
ctcccacgct gccctcctgc ctgcagccat gacgcccctg ctcaccctga tcctggtggt     660
cctcatgggc ttacctctgg cccaggcctt ggactgccac gtgtgtgcct acaacggaga     720
caactgcttc aacccccatgc gctgcccggc tatggttgcc tactgcatga ccacgcgcac     780
ctactacacc cccaccagga tgaaggtcag taagtcctgc gtgccccgct gcttcgagac     840
tgtgtatgat ggctactcca agcacgcgtc caccacctcc tgctgccagt acgacctctg     900
```

```
caacggcacc ggccttgcca ccccggccac cctggccctg cccccatcc tcctggccac    960 cctctgggt ctcctctaaa gccccgagg cagacccact caagaacaaa gctctcgaga    1020
cacactgcta caccctcgca cccagctcac cctgcctcac cctccacact ccctgcgacc    1080
tcctcagcca tgcccagggt caggactgtg ggcaagaaga cacccgacct ccccaacca    1140 ccacacgacc tcacttcgag gccttgacct ttcgatgctg tgtgggatcc caaaagtgtc    1200
cggctttgat gggctgatca gcccctcgcc tgtccagggc tatttatggg gaggggccca    1260
gtcaggcagg gagcactgag cagatgggag ctgtggccaa gcccaccttc tgggaagccc    1320
taggagaggc ccctgcctca gtctgcccct ggtgtgctgg ggcaggggga agacaaggaa    1380
tgcccgcagg tggggtggtg gggagactct taggaggaaa ggctcctcca ggcctagtca    1440
cgcttcctac tgaggccagg agctgccagg accggtacgg gatcagggct gtgggaggag    1500
ggcctttggc accggcccct gtgctaggaa gtctgccagg cccgagttgg agccaccccc    1560
tgcaggggag gggcggctc tgcctcagca ggccccaggg ccccgaagt cacagaagct    1620 ttttcgggtc cagcaagggg tgtgtgtcct ctcagtcaaa cccttgacg tttcccaccc    1680 cctcacgggg agggcaccag gcctgaagct ggcaggagct agggccatgc tatatttggt    1740
gggtcctgga cgctgacccg ccagcgcta ttctgggcag ggagggaaag gggcagagca    1800
ggtggtcccc cgagtcctgg tccccaacca cagcaggacc cagccgagca aggcaaaaga    1860
cgcaggactg ggggatgcgc gcacaggctg ggggttggga gcagcctggg gccggcgcgg    1920
gcctgggcgt gggaaggcgg agcatgccac cctctcgtgg ccgtgcgggg gcgggagtgg    1980
ggagggtggg gtgggagggg cggagaccca gccctcccc cgcagcggga tgcgcacagt    2040
gagtgggtcc ctccatcacc ttccacctgg ggatgcaccc actgggaggg cagggtggaa    2100
gccccagctg ggtgtgtgga ctcccaggga ccccacccca ggcctgggaa gcagggtca    2160 gcccaacacg caccaatcca tccccgatgc aggtagccca gggagcacct gccctgctg    2220 tgaatggggc attcggggc gtgagacctt ttggtgccag cggtcacgct gcacctgagg    2280
cccccacctg accagtgctc ccagctctgg tgtcctgaga aacccttcaa gccatcccgc    2340
atgggcagga tggtgacata tccatgtggt aggattgtcc cggccccaaa gtatggccct    2400
ggtcagggga gccctgctg gaaattgcat ctccagagct ttgatgcagg acccctgggg    2460 gatcaggaa tgagggtctc caccccaggg gtctccttgc agtgagtcta tatgcaggcc    2520
tgcgttctgc tcctggggct ggttctgagt gcccagcttc agtctcctga aacatgagg    2580 atgggagggg gcagagtctt gctgagggca cacccagttc ccgctggagg aggacagtgc    2640
cagtcttctg caaagggacc ttgggtggga acgggcccgg agcgggagga acgtgactcc    2700
ccagagggaa gatgggcatc atactgggcc cagagctggg aaggagttgc tgccagcaca    2760
gggtgggcct ggactcccct cgccctaccc ccagtggtt gtggctgtag ccctaagcct    2820
ggagagcagg accggcccgg ggtgtctggg aggctgccag gtgcctccca gagctcccaa    2880
gggcccccac ctgcaagtgc cagcctcagg gcagtgccca aatgaggccc tctcagctgc    2940
agccagcgat gccttgggat gcttaccggg agggaggcgg cttgggctc ctaagtcctt    3000 gggagaggct gggagcagtc actgcgcggc ttgcgcaagc ccattgtcgg gttgggtggc    3060
ttcctcagcc agggctggga ggactccag gatcaggtcc tccctgtctc gagtctcagt    3120 gggtgatgg ggaggagacc tggccaccca tggctcaggg gcagctgaga acaaggacct    3180
gctggagctg gaagtgctgt ggtgttgagg ggtggggtgg gcagcttctc acacctgcct    3240
```

```
cctgcctcct tctgtccacc tttccaccac cctgacctgt cccagcccca cacatggttc    3300
tgcctggctg gcctgccctt ggcacctggc gtagagcaca cagaaggcac tcagctaatg    3360
ctgggcaggc ccactcatgg ggagtgcgtg gctgtgcagc accagggaac cggcacagca    3420
gcgccggcag aaatcacagc agtaaacttg tccgggttgt atgcatcaag gtggcgatgg    3480
acgtgggtcc ccccactgca ctgtggccct gagcactgta tagcagcccg gcaatgggag    3540
ccattatctt gccctttga cagaggagga cacagaggca cagggaggtg aagtagctgc    3600
cccacactag tgcctcctcg ctcactcacc accccctgca ccacagtgca gccgcttctc    3660
ccaccagctg gggttccttg accccaag cctgggaagg gggaggtgag tttacaaaat    3720
ggaaagctta aaggagaaa agtggaacca gaggtttgag aagccctgag tggtagagta    3780
aggcctccag cgctgcctct gggtgcaggg cagagtggca gaggagaggg ggagaggcac    3840
tgggcaccat gggggcccag ttcccacttc ggggatctct ctcgcagaac cgagggtccc    3900
cttcatgggg gtagatgccc agggctagct gttgccactg tctgtgtgga cctgagtcct    3960
ggacatgccc gagtgactca ggagtggctg cttgggcggg ctctgtcacc ctaggatgtt    4020
atacattctg ggaactggac aggagtggct gcttgggcgg gctctggcac cctgggatgt    4080
tatacattct gggaactgga caggagtggc tgcttgggtg gctctggca ccctgggatg    4140 ttatacattc tgggaactgc aatcagccac tagagaagtc ggagctacag gaagtgaccc    4200
tggggtggga cctgggaaca tggccaggtc agcatgggga cacccggctc cagcaggagc    4260
tctggtctgt cctggggtct ttgggggcag ggctgcggcc ctgggcaggc ttcctccagg    4320
cggaggtcct ggggaagtgg gggagccagg ccagctgccg cctcccccac tatgtagcat    4380
ctgattcgtc atctctcatg aaggcgattt ggttcataac tctgaaactc tgaaaaaggt    4440
caaaagaagc agagaggccc tcggtggata tgccagcttt tctgccggtg ctttctccca    4500
ctactctggg tggtctgctc tcctcttcaa acctcagctc gcaggagggg cctgaatctg    4560
ccagcccctc aggatctcct tccctctggg ccctccccag ccttaaggag cctcccagac    4620
agaagggtgg acagagccac ctgggcagcc cgagagacac acggggggtcc tccctgtgga    4680 cagcccctgcc agcttccgcc cagccctgag cttcatttgc atcttgagga gtaagggggtg    4740 gtgaaatggg aatgctggtc tggctcagct ggtcgtgggc ataagtgccc gctgaatgga    4800
tggcatctct ccctcctgtc ttatgttctg gggtccaggt gcttcccagg gccatgcccc    4860
tgctgctaat gcttgcccta acccttaccc taaccagcgt ccagcgtcgt ctcaccgagc    4920
cgtaaataaa tcaacagatt cgcattgtca aaaaaaaaaa aaaaaaa              4967
```

<210> SEQ ID NO 5
<211> LENGTH: 97
<212> TYPE: PRT
<213> ORGANISM: Homo sapiens

<400> SEQUENCE: 5

Met Gln Leu Gly Thr Gly Leu Leu Leu Ala Ala Val Leu Ser Leu Gln
1               5                   10                  15

Leu Ala Ala Ala Glu Ala Ile Trp Cys His Gln Cys Thr Gly Phe Gly
                20                  25                  30

Gly Cys Ser His Gly Ser Arg Cys Leu Arg Asp Ser Thr His Cys Val
            35                  40                  45

Thr Thr Ala Thr Arg Val Leu Ser Asn Thr Glu Asp Leu Pro Leu Val
        50                  55                  60

Thr Lys Met Cys His Ile Gly Cys Pro Asp Ile Pro Ser Leu Gly Leu

Gly Pro Tyr Val Ser Ile Ala Cys Cys Gln Thr Ser Leu Cys Asn His
65              70                  75                  80

Asp
            85                  90                  95

<210> SEQ ID NO 6
<211> LENGTH: 589
<212> TYPE: DNA
<213> ORGANISM: Homo sapiens

<400> SEQUENCE: 6
agcccgacct caccaggaga acatgcagct cggcactggg ctcctgctgg ccgccgtcct    60
gagcctgcag ctggctgcag ccgaagccat atggtgtcac cagtgcacgg gcttcggagg   120
gtgctcccat ggatccagat gcctgaggga ctccacccac tgtgtcacca ctgccacccg   180
ggtcctcagc aacaccgagg atttgcctct ggtcaccaag atgtgccaca taggctgccc   240
cgatatcccc agcctgggcc tgggccccta cgtatccatc gcttgctgcc agaccagcct   300
ctgcaaccat gactgacggc tgccctcctc aggcccccg dacgctcagc cccacagcc    360 cccacagcct ggcgccaggg ctcacagctg cccctccctc gagactggcc agcccacctc   420
tcccggcctc tgcagccacc gtccagcacc gcttgtccta gggaagtcct gcgtggagtc   480
ttgcctcaat ctgctgccgt ccaagcctgg ggcccatcgt gcctgccgcc ccttcaggtc   540
ccgacctccc cacaataaaa tgtgattgga tcgtgtggta caaaaaaaa              589

<210> SEQ ID NO 7
<211> LENGTH: 116
<212> TYPE: PRT
<213> ORGANISM: Homo sapiens

<400> SEQUENCE: 7

Met Thr Pro Leu Leu Thr Leu Ile Leu Val Val Leu Met Gly Leu Pro
1               5                   10                  15

Leu Ala Gln Ala Leu Asp Cys His Val Cys Ala Tyr Asn Gly Asp Asn
            20                  25                  30

Cys Phe Asn Pro Met Arg Cys Pro Ala Met Val Ala Tyr Cys Met Thr
        35                  40                  45

Thr Arg Thr Tyr Tyr Thr Pro Thr Arg Met Lys Val Ser Lys Ser Cys
    50                  55                  60

Val Pro Arg Cys Phe Glu Thr Val Tyr Asp Gly Tyr Ser Lys His Ala
65              70                  75                  80

Ser Thr Thr Ser Cys Cys Gln Tyr Asp Leu Cys Asn Gly Thr Gly Leu
            85                  90                  95

Ala Thr Pro Ala Thr Leu Ala Leu Ala Pro Ile Leu Leu Ala Thr Leu
            100                 105                 110

Trp Gly Leu Leu
        115

<210> SEQ ID NO 8
<211> LENGTH: 4609
<212> TYPE: DNA
<213> ORGANISM: Homo sapiens

<400> SEQUENCE: 8
agggggttgg gaagctcgaa gccgcaggcc tgactctggc ctttggcatc ctggggttgg    60
cctgggcaaa tgtgtcgtga gagacggatt tgttgttctc gggaaggcgg ttgcagcact   120

```
cccagtagac caggagctcc gggaggcagg gccggcccca cgtcctctgc gcaccaccct      180
gagttggatc tctgtgcgc cacctgagtt ggatccaggg ctagctgctg ttgacctccc       240
cactcccacg ctgccctcct gcctgcagcc atgacgcccc tgctcaccct gatcctggtg      300
gtcctcatgg gcttacctct ggcccaggcc ttggactgcc acgtgtgtgc ctacaacgga      360
gacaactgct tcaaccccat gcgctgcccg gctatggttg cctactgcat gaccacgcgc      420
acctactaca cccccaccag gatgaaggtc agtaagtcct gcgtgccccg ctgcttcgag      480
actgtgtatg atggctactc caagcacgcg tccaccacct cctgctgcca gtacgacctc      540
tgcaacggca ccggccttgc caccccggcc accctggccc tggcccccat cctcctggcc      600
accctctggg gtctcctcta aagcccccga ggcagaccca ctcaagaaca aagctctcga      660
gacacactgc tacaccctcg cacccagctc accctgcctc accctccaca ctccctgcga      720
cctcctcagc catgcccagg gtcaggactg tgggcaagaa gacacccgac ctcccccaac      780
caccacacga cctcacttcg aggccttgac ctttcgatgc tgtgtgggat cccaaaagtg      840
tccggctttg atgggctgat cagcccctcg cctgtccagg gctatttatg gggaggggcc      900
cagtcaggca gggagcactg agcagatggg agctgtggcc aagcccacct tctgggaagc      960
cctaggagag gccccctgcct cagtctgccc ctggtgtgct ggggcagggg gaagacaagg     1020
aatgcccgca ggtggggtgg tggggagact cttaggagga aaggctcctc caggcctagt     1080
cacgcttcct actgaggcca ggagctgcca ggaccggtac gggatcaggg ctgtggggag     1140
agggcctttg gcaccggccc ctgtgctagg aagtctgcca ggcccgagtt ggagccaccc     1200
cctgcagggg aggggcggc tctgcctcag caggccccag gccccccgaa gtcacagaag      1260
ctttttcggg tccagcaagg ggtgtgtgtc ctctcagtca aacccctga cgtttcccac      1320 cccctcacgg ggagggcacc aggcctgaag ctggcaggag ctaggccat gctatatttg      1380 gtgggtcctg gacgctgacc cggccagcgc tattctgggc agggagggaa aggggcagag     1440
caggtggtcc cccgagtcct ggtccccaac cacagcagga cccagccgag caaggcaaaa     1500
gacgcaggac tgggggatgc gcgcacaggc tgggggttgg gagcagcctg gggccggcgc     1560
gggcctgggc gtgggaaggc ggagcatgcc accctctcgt ggccgtgcgg gggcgggagt     1620
ggggagggtg gggtggggag ggcggagacc cagcccctcc cccgcagcgg gatgcgcaca     1680
gtgagtgggt ccctccatca ccttccacct ggggatgcac ccactgggag ggcagggtgg     1740 aagcccagc tgggtgtgtg gactcccagg gaccccaccc caggcctggg aagcaggggt      1800
cagcccaaca cgcaccaatc catccccgat gcaggtagcc cagggagcac ctgcccctgc     1860
tgtgaatggg gcattcgggg gcgtgagacc ttttggtgcc agcggtcacg ctgcacctga    1920
ggcccccacc tgaccagtgc tcccagctct ggtgtcctga aaaccccttc aagccatccc     1980
gcatgggcag gatggtgaca tatccatgtg gtaggattgt cccggcccca agtatggcc     2040 ctggtcaggg gagcccctgc tggaaattgc atctccagag cttttgatgca ggaccccgg    2100 gggatcaggg aatgagggtc tccacccag gggtctcctt gcagtgagtc tatatgcagg     2160
cctgcgttct gctcctgggg ctggttctga gtgcccagct tcagtctcct gagaacatga     2220
ggatgggagg gggcagagtc ttgctgaggg cacacccagt tcccgctgga ggaggacagt    2280
gccagtcttc tgcaaaggga ccttgggtgg gaacgggccc ggagcgggag gaacgtgact     2340
ccccagaggg aagatgggca tcatactggg cccagagctg ggaaggagtt gctgccagca     2400
cagggtgggc ctggactccc ctcgccccta cccccagtgg ttgtggctgt agccctaagc     2460
ctggagagca ggaccggccc ggggtgtctg ggaggctgcc aggtgcctcc cagagctccc    2520
```

```
aagggccccc acctgcaagt gccagcctca gggcagtgcc caaatgaggc cctctcagct    2580
gcagccagcg atgccttggg atgcttaccg ggagggaggc ggctttgggc tcctaagtcc    2640
ttgggagagg ctgggagcag tcactgcgcg gcttgcgcaa gcccattgtc gggttgggtg    2700
gcttcctcag ccagggctgg gagggactcc aggatcaggt cctccctgtc tcgagtctca    2760
gtggggtgat ggggaggaga cctggccacc catggctcag gggcagctga aacaaggac    2820 ctgctggagc tggaagtgct gtggtgttga ggggtgggt gggcagcttc tcacacctgc     2880
ctcctgcctc cttctgtcca ccttttccacc accctgacct gtcccagccc cacacatggt   2940
tctgcctggc tggcctgccc ttggcacctg gcgtagagca cacagaaggc actcagctaa    3000
tgctgggcag gcccactcat ggggagtgcg tggctgtgca gcaccaggga accggcacag    3060
cagcgccggc agaaatcaca gcagtaaact tgtccgggtt gtatgcatca aggtggcgat    3120
ggacgtgggt ccccccactg cactgtggcc ctgagcactg tatagcagcc cggcaatggg    3180
agccattatc ttgccccttt gacagaggag gacacagagg cacagggagg tgaagtagct    3240
gccccacact agtgcctcct cgctcactca ccaccccctg caccacagtg cagccgcttc    3300
tcccaccagc tggggttcct tggacccccca agcctgggaa gggggaggtg agtttacaaa   3360
atggaaagct taaaggaga aaagtggaac cagaggtttg agaagccctg agtggtagag     3420
taaggcctcc agcgctgcct ctgggtgcag ggcagagtgg cagaggagag ggggagaggc    3480
actgggcacc atgggggccc agttcccact tcggggatct ctctcgcaga accgagggtc    3540
cccttcatgg gggtagatgc ccagggctag ctgttgccac tgtctgtgtg gacctgagtc    3600
ctggacatgc ccgagtgact caggagtggc tgcttgggcg ggctctgtca ccctaggatg    3660
ttatacattc tgggaactgg acaggagtgg ctgcttgggc gggctctggc acctgggat    3720 gttatacatt ctgggaactg gacaggagtg gctgcttggg tgggctctgg cacctcggga   3780
tgttatacat tctgggaact gcaatcagcc actagagaag tcggagctac aggaagtgac    3840
cctggggtgg gacctgggga catggccagg tcagcatggg gacacccggc tccagcagga    3900
gctctggtct gtcctggggt ctttgggggc agggctgcgg ccctgggcag gcttcctcca    3960
ggcggaggtc ctggggaagt gggggagcca ggccagctgc cgcctccccc actatgtagc    4020
atctgattcg tcatctctca tgaaggcgat ttggttcata actctgaaac tctgaaaaag    4080
gtcaaaagaa gcagagaggc cctcggtgga tatgccagct tttctgccgg tgctttctcc    4140
cactactctg ggtggtctgc tctcctcttc aaacctcagc tcgcagggag ggcctgaatc    4200
tgccagcccc tcaggatctc cttccctctg ggccctcccc agccttaagg agcctcccag    4260
acagaagggt ggacagagcc acctgggcag cccgagagac acacggggt cctccctgtg     4320 gacagccctg ccagcttccg cccagccctg agcttcattt gcatcttgag gagtaagggg    4380
tggtgaaatg ggaatgctgg tctggctcag ctggtcgtgg gcataagtgc ccgctgaatg    4440
gatggcatct ctccctcctg tcttatgttc tggggtccag gtgcttccca gggccatgcc    4500
cctgctgcta atgcttgccc taaccccttac cctaaccagc gtccagcgtc gtctcaccga    4560
gccgtaaata aatcaacaga ttcgcattgt caaaaaaaaa aaaaaaaaa              4609
```

<210> SEQ ID NO 9
<211> LENGTH: 116
<212> TYPE: PRT
<213> ORGANISM: Homo sapiens

<400> SEQUENCE: 9

```
Met Thr Pro Leu Leu Thr Leu Ile Leu Val Leu Met Gly Leu Pro
1               5                   10                  15

Leu Ala Gln Ala Leu Asp Cys His Val Cys Ala Tyr Asn Gly Asp Asn
            20                  25                  30

Cys Phe Asn Pro Met Arg Cys Pro Ala Met Val Ala Tyr Cys Met Thr
            35                  40                  45

Thr Arg Thr Tyr Tyr Thr Pro Thr Arg Met Lys Val Ser Lys Ser Cys
        50                  55                  60

Val Pro Arg Cys Phe Glu Thr Val Tyr Asp Gly Tyr Ser Lys His Ala
65                  70                  75                  80

Ser Thr Thr Ser Cys Cys Gln Tyr Asp Leu Cys Asn Gly Thr Gly Leu
                85                  90                  95

Ala Thr Pro Ala Thr Leu Ala Leu Ala Pro Ile Leu Leu Ala Thr Leu
            100                 105                 110

Trp Gly Leu Leu
        115

<210> SEQ ID NO 10
<211> LENGTH: 4724
<212> TYPE: DNA
<213> ORGANISM: Homo sapiens

<400> SEQUENCE: 10
ggggccgggg caggcctggg gcggggcctg cggtgagctc gcgctgggcg ggctgttccg      60
ggggcgggac tgggctgggc ctgcggtgag catcaggcga tgcggcacgg gtgctgcggg     120
acacacagac acgcctacga ttagactcag gcaggcacct accggcgagc ggccgcgggt     180
gactcccagg cgcggcggta cctcacggtg gtgaaggtca cagggttgca gcactcccag     240
tagaccagga gctccgggag gcagggccgg ccccacgtcc tctgcgcacc accctgagtt     300
ggatcctctg tgcgccacct gagttggatc cagggctagc tgctgttgac ctccccactc     360
ccacgctgcc ctcctgcctg cagccatgac gcccctgctc accctgatcc tggtggtcct     420
catgggctta cctctggccc aggccttgga ctgccacgtg tgtgcctaca acggagacaa     480
ctgcttcaac cccatgcgct gcccggctat ggttgcctac tgcatgacca cgcgcaccta     540
ctacaccccc accaggatga aggtcagtaa gtcctgcgtg ccccgctgct cgagactgt      600 gtatgatggc tactccaagc acgcgtccac cacctcctgc tgccagtacg acctctgcaa     660
cggcaccggc cttgccaccc cggccaccct ggccctggcc ccatcctcc tggccaccct     720 ctggggtctc ctctaaagcc cccgaggcag acccactcaa gaacaaagct ctcgagacac     780
actgctacac cctcgcaccc agctcaccct gcctcaccct ccacactccc tgcgacctcc     840
tcagccatgc ccagggtcag gactgtgggc aagaagacac ccgacctccc ccaaccacca     900
cacgacctca cttcgaggcc ttgacctttc gatgctgtgt gggatcccaa aagtgtccgg     960
ctttgatggg ctgatcagcc cctcgcctgt ccagggctat ttatggggag ggcccagtc    1020 aggcagggag cactgagcag atgggagctg tggccaagcc caccttctgg gaagccctag    1080
gagaggcccc tgcctcagtc tgccctggt gtgctgggc aggggaaga caaggaatgc     1140 ccgcaggtgg ggtggtgggg agactcttag gaggaaaggc tcctccaggc ctagtcacgc    1200
ttcctactga ggccaggagc tgccaggacc ggtacgggat cagggctgtg ggaggagggc    1260
ctttggcacc ggccctgtg ctaggaagtc tgccaggccc gagttggagc cacccctgc     1320 aggggagggg gcggctctgc ctcagcaggc cccaggccc ccgaagtcac agaagctttt    1380
tcgggtccag caagggggtgt gtgtcctctc agtcaaaccc cttgacgttt cccacccct     1440
```

```
cacggggagg gcaccaggcc tgaagctggc aggagctagg gccatgctat atttggtggg   1500
tcctggacgc tgacccggcc agcgctattc tgggcaggga gggaaagggg cagagcaggt   1560
ggtcccccga gtcctggtcc ccaaccacag caggacccag ccgagcaagg caaaagacgc   1620
aggactgggg gatgcgcgca caggctgggg gttgggagca gcctggggcc ggcgcgggcc   1680
tgggcgtggg aaggcggagc atgccaccct ctcgtggccg tgcgggggcg ggagtgggga   1740
gggtggggtg gggagggcgg agacccagcc cctccccgc agcgggatgc gcacagtgag    1800
tgggtccctc catcaccttc cacctgggga tgcacccact ggagggcag ggtggaagcc    1860 ccagctgggt gtgtggactc ccagggaccc caccccaggc ctgggaagca ggggtcagcc   1920
caacacgcac caatccatcc ccgatgcagg tagcccaggg agcacctgcc cctgctgtga   1980
atggggcatt cggggggcgtg agaccttttg gtgccagcgg tcacgctgca cctgaggccc   2040
ccacctgacc agtgctccca gctctggtgt cctgagaaac ccttcaagcc atcccgcatg   2100
ggcaggatgg tgacatatcc atgtggtagg attgtcccgg ccccaaagta tggccctggt   2160
caggggagcc cctgctggaa attgcatctc cagagctttg atgcaggacc cctgggggat   2220
cagggaatga gggtctccac cccagggggtc tccttgcagt gagtctatat gcaggcctgc   2280
gttctgctcc tggggctggt tctgagtgcc cagcttcagt ctcctgagaa catgaggatg   2340 ggaggggggca gagtcttgct gagggcacac ccagttcccg ctggaggagg acagtgccag   2400
tcttctgcaa agggaccttg ggtgggaacg ggcccggagc gggaggaacg tgactcccca   2460
gagggaagat gggcatcata ctgggcccag agctgggaag gagttgctgc cagcacaggg   2520
tgggcctgga ctcccctcgc ccctacccccc agtggttgtg gctgtagccc taagcctgga   2580
gagcaggacc ggcccgggt gtctggggagg ctgccaggtg cctcccagag ctcccaaggg   2640
cccccacctg caagtgccag cctcagggca gtgcccaaat gaggccctct cagctgcagc   2700
cagcgatgcc ttgggatgct taccgggagg gaggcggctt tgggctccta agtccttggg   2760
agaggctggg agcagtcact gcgcggcttg cgcaagccca ttgtcgggtt gggtggcttc   2820
ctcagccagg gctgggaggg actccaggat caggtcctcc ctgtctcgag tctcagtggg   2880
gtgatgggga ggagacctgg ccacccatgg ctcagggca gctgagaaca aggacctgct   2940
ggagctggaa gtgctgtggt gttgaggggt ggggtgggca gcttctcaca cctgcctcct   3000
gcctccttct gtccacctttt ccaccaccct gacctgtccc agcccacac atggttctgc   3060 ctggctggcc tgcccttggc acctggcgta gagcacacag aaggcactca gctaatgctg   3120
ggcaggccca ctcatgggga gtgcgtggct gtgcagcacc agggaaccgg cacagcagcg   3180
ccggcagaaa tcacagcagt aaacttgtcc gggttgtatg catcaaggtg gcgatggacg   3240
tgggtccccc cactgcactg tggccctgag cactgtatag cagcccggca atgggagcca   3300
ttatcttgcc cctttgacag aggaggacac agaggcacag ggaggtgaag tagctgcccc   3360
acactagtgc ctcctcgctc actcaccacc cctgcaccca cagtgcagcc gcttctccca   3420
ccagctgggg ttccttggac ccccaagcct gggaaggggg aggtgagttt acaaaatgga   3480
aagcttaaaa ggagaaaagt ggaaccagag gtttgagaag ccctgagtgg tagagtaagg   3540
cctccagcgc tgcctctggg tgcagggcag agtggcagag gagaggggga gaggcactgg   3600
gcaccatggg ggcccagttc ccacttcggg gatctctctc gcagaaccga gggtcccctt   3660
catgggggta gatgcccagg gctagctgtt gccactgtct gtgtggacct gagtcctgga   3720
catgcccgag tgactcagga gtggctgctt gggcgggctc tgtcaccta ggatgttata    3780
```

-continued

```
cattctggga actggacagg agtggctgct tgggcgggct ctggcaccct gggatgttat   3840
acattctggg aactggacag gagtggctgc ttgggtgggc tctggcaccc tgggatgtta   3900
tacattctgg gaactgcaat cagccactag agaagtcgga gctacaggaa gtgaccctgg   3960
ggtgggacct ggggacatgg ccaggtcagc atggggacac ccggctccag caggagctct   4020
ggtctgtcct ggggtctttg ggggcagggc tgcggccctg ggcaggcttc ctccaggcgg   4080
aggtcctggg gaagtggggg agccaggcca gctgccgcct cccccactat gtagcatctg   4140
attcgtcatc tctcatgaag gcgatttggt tcataactct gaaactctga aaaaggtcaa   4200
aagaagcaga gaggccctcg gtggatatgc cagcttttct gccggtgctt tctcccacta   4260
ctctgggtgg tctgctctcc tcttcaaacc tcagctcgca gggagggcct gaatctgcca   4320
gcccctcagg atctccttcc ctctgggccc tccccagcct taaggagcct cccagacaga   4380
agggtggaca gagccacctg ggcagcccga gagacacacg ggggtcctcc ctgtggacag   4440
ccctgccagc ttccgcccag ccctgagctt catttgcatc ttgaggagta aggggtggtg   4500
aaatgggaat gctggtctgg ctcagctggt cgtgggcata agtgcccgct gaatggatgg   4560
catctctccc tcctgtctta tgttctgggg tccaggtgct tcccagggcc atgccctgc    4620 tgctaatgct tgccctaacc cttaccctaa ccagcgtcca gcgtcgtctc accgagccgt   4680
aaataaatca acagattcgc attgtcaaaa aaaaaaaaaa aaaa                    4724
```